United States Patent
Leveille et al.

(10) Patent No.: US 10,386,344 B2
(45) Date of Patent: Aug. 20, 2019

(54) STRAIN INDUCED FACE SEAL

(71) Applicant: Waters Technology Corporation, Milford, MA (US)

(72) Inventors: Wade P. Leveille, Douglas, MA (US); Mathew H. DeLano, Allston, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 16/003,505

(22) Filed: Jun. 8, 2018

(65) Prior Publication Data
US 2018/0356376 A1    Dec. 13, 2018

Related U.S. Application Data

(60) Provisional application No. 62/518,306, filed on Jun. 12, 2017.

(51) Int. Cl.
| | |
|---|---|
| *G01N 30/60* | (2006.01) |
| *F16L 9/14* | (2006.01) |
| *B21C 37/06* | (2006.01) |
| *F16L 13/14* | (2006.01) |
| *F16L 13/16* | (2006.01) |

(52) U.S. Cl.
CPC ......... *G01N 30/6039* (2013.01); *B21C 37/06* (2013.01); *F16L 9/14* (2013.01); *F16L 13/141* (2013.01); *F16L 13/161* (2013.01); *G01N 30/6026* (2013.01); *G01N 30/6065* (2013.01)

(58) Field of Classification Search
CPC ........... G01N 30/6026; G01N 30/6039; G01N 30/6065
See application file for complete search history.

(56) References Cited

U.S. PATENT DOCUMENTS

| | | | |
|---|---|---|---|
| 4,277,091 A | 7/1981 | Hunter | |
| 2011/0278214 A1* | 11/2011 | Benevides | B01D 15/22 |
| | | | 210/198.2 |

(Continued)

FOREIGN PATENT DOCUMENTS

WO    98/46924 A1    10/1998

OTHER PUBLICATIONS

Application No. PCT/US2018/036702, International Search Report and the Written Opinion dated Aug. 13, 2018. 12 pages.

*Primary Examiner* — Daniel S Larkin
(74) *Attorney, Agent, or Firm* — Schmeiser, Olsen & Watts LLP

(57) ABSTRACT

The invention relates to tubing assemblies and methods for forming a fluidic connection to make the same. The assemblies include an outer tube having disposed therein a first inner tube affixed to the outer tube, a second inner tube and a support tube disposed in the second inner tube. The second inner tube is abutted against the first inner tube. A radial crimp is made in the outer tube over the second inner tube a distance x from where the tubes abut; the distance x being such that the end of the second inner tube seals against the end of the first inner tube. Various embodiments provide assemblies suitable for use with high fluidic pressure (e.g., greater than an about 70 MPa, approximately about 10,000 psi) and formation of chromatographic column assemblies comprising a capillary tube predisposed within the first or second inner tube prior to formation of the seal.

46 Claims, 14 Drawing Sheets

(56) References Cited

U.S. PATENT DOCUMENTS

2012/0061955 A1 3/2012 Hochgraeber et al.
2013/0126021 A1 5/2013 Hobbs
2013/0334118 A1 12/2013 Reinhardt
2014/0166562 A1 6/2014 Michienzi et al.

* cited by examiner

STRAIN INDUCED FACE SEAL

RELATED APPLICATIONS

This application is a non-provisional patent application claiming priority to U.S. Provisional Patent Application No. 62/518,306, filed Jun. 12, 2017, entitled "Strain Induced Face Seal," which is incorporated herein by reference.

FIELD OF THE INVENTION

The inventions relate generally to fluidic seals such as those used in joining tubing assemblies. In various embodiments, the inventions relate to high pressure tubing assemblies.

BACKGROUND

Various types or forms of fluidic conduits, such as tubes, columns and linear flow cells are used in analytical instrumentation for transporting and/or processing fluids and samples. The conduits in such systems often include tubing assemblies where different conduits are coupled together to form fluidic connections between them.

Fluidic conduits employed in chemical analysis instruments, such as, for example, chromatography (LC), high performance liquid chromatography (HPLC), ultra performance liquid chromatography (UPLC®), capillary electrophoresis (CE) and capillary electro-chromatography (CEC), can have demanding performance criteria. For example, a liquid chromatography system, such as a system designed for ultra performance liquid chromatography (UPLC®), can operate at pressure that may exceed 18,000 psi.

Problems associated with forming fluidic connections between tubing assemblies are particularly prominent for those required to withstand high-pressure operation, for example, pressures in the range 10,000 to 18,000 pounds per square inch (psi), and for systems where the tubing dimensions are small, for example where the area of the tubing endface is large relative to the area of the tubing opening and/or where the thickness of the tubing wall is large relative to the tubing inner diameter.

A primary concern in high pressure fluidic systems is leaks where two different tubes are coupled. In typical couplings, the seal is formed along the side of the tube. For example, many couplings use an annular sealing element such as a ferrule that has a conical outer surface. To form a fluid-tight coupling, a tube having the annular sealing element displaced away from the endface is inserted into a receptacle of a coupling body. The receptacle is defined by a cylindrical bore that transitions to a conical bore and then to a smaller diameter cylindrical bore. A fluid channel extends from the surface at the bottom of the smaller diameter cylindrical bore into the coupling body. The cone angle of the conical bore is greater than the cone angle of the annular sealing element resulting in a seal along the circumferential contact between the annular sealing element and the conical surface of the conical bore. Additional force applied by a compression screw after achieving initial contact between the annular sealing element and conical bore surface results in a contact seal between the annular sealing element and the outer surface of the tube. If the endface of the tube is not in contact with the bottom of the cylindrical bore, the region between the outer surface of the tube and the side wall of the smaller cylindrical bore below the circumferential contact seal represents a dead volume, e.g., a volume that is unswept or only partially swept by the flowing fluid. Such dead volumes can result, among other things, in sample entrapment and carry-over. However, such circumferential seals allow for greater control of the sealing process which can be critical when elements such as silica capillary tubes are used.

An analytical technique that relies upon accurate flow volumes, accurate sample concentrations and/or reproducibility will be adversely affected by dead volume. In chromatography adverse effects such as carryover and peak tailing can result from the use of conventional couplings used to achieve fluid-tight seals. The introduction of dead volume can be especially detrimental for tubing of smaller dimensions as such dead volumes can become proportionally larger as the tubing dimensions decrease.

SUMMARY

In various aspects and embodiments, the present inventions provide, for example, tubing assemblies, chromatographic column assemblies, and methods form formation of fluidic connections between two fluidic conduits that can address the problem of dead volume in the fluidic connections.

In one aspect, the invention features a tube assembly where a face seal is formed between the ends of two tubes. In various embodiments the tubing assembly comprises an outer tube with a first inner tube and a second inner tube disposed therein, the first inner tube having a first end and a second end and the second inner tube having a first end and a second end, where the second end of the second inner tube abuts against the first end of the first inner tube. The area of contact between the second end of the second inner tube and the first end of the first inner tube defines an end interface. Additionally, a support tube is disposed within the second inner tube, the support tube being more resistant to deformation by radial compression than the second inner tube. The outer tube has two radial crimps, a first radial crimp and a second radial crimp, where the first radial crimp is at a longitudinal location along the outer tube in a direction away from the end interface towards the first end of the second inner tube at a distance x from the end interface and the second radial crimp is at a longitudinal location along the outer tube in the direction of the first radial crimp and further away from the end interface than the first radial crimp, and in various embodiments between the first radial crimp and the first end of the second tube. The distance x is such that deformation of the outer tube to create the first radial crimp forms a fluid-tight seal between the second end of the second inner tube and the first end of the first inner tube at the end interface. In various embodiments, the tubing assembly has a third radial crimp at a longitudinal location along the outer tube in a direction away from the end interface towards the second end of the first inner tube.

In various embodiments, the tubing assembly further comprises additional tubes disposed in the lumen of the first inner tube, the support tube, or both. For example, a capillary tube filled with a sorbent bed can be disposed in the second inner tube. The sorbent bed can be of a variety of materials, such as, for example, those used for filtration, ion exchange, chromatographic separation, and the like.

In one aspect, the invention features a chromatographic column assembly, comprising an outer tube disposed around a first inner tube and a second inner tube, the first inner tube having a first end and a second end and the second inner tube having a first end and a second end, where the second end of the second inner tube abuts against the first end of the first inner tube. The area of contact between the second end of the second inner tube and the first end of the first inner tube defines an end interface. Additionally, a support tube is disposed within the second inner tube, the support tube being more resistant to deformation by radial compression than the second inner tube, and a sorbent bed is disposed in the lumen of the first inner tube, the lumen of the support tube, or both. The outer tube has at least two radial crimps, a first radial crimp and a second radial crimp, where the first radial crimp is at a longitudinal location along the outer tube in a direction away from the end interface towards the first end of the second inner tube at a distance x from the end interface. The second radial crimp is at a longitudinal location along the outer tube in the direction of the first radial crimp and further away from the end interface than the first radial crimp, and in various embodiments between the first radial crimp and the first end of the second tube. The distance x is such that deformation of the outer tube to create the first radial crimp forms a fluid-tight seal between the second end of the second inner tube and the first end of the first inner tube at the end interface.

In various embodiments, a chromatographic column assembly further includes: a third inner tube inside the lumen of the first inner tube and a chromatographic media within the lumen of the third inner tube; a fourth inner tube inside the lumen of the support tube and a chromatographic media within the lumen of the fourth inner tube; or both.

In the present inventions, the support tube extends at least from the first end of the first inner tube and at least past the first radial crimp. In various embodiments, the support tube extends into the lumen of the first inner tube. In various embodiments, the support tube extends past the second radial crimp. The support tube can be of a variety of materials and is selected to be comprised of a material more resistant to radial compression than the material of the second inner tube, such that, for example, upon formation of the first radial crimp the support tube substantially limits deformation of the second inner tube radially into the second inner tube lumen in the region about the first radial crimp. In various embodiments, the support tube is comprised of a material having a Young's modulus that is greater than the Young's modulus of the material comprising the second inner tube.

In the present inventions, the second inner tube is made of a polymeric material and the outer tube is made of a metal (e.g., a stainless steel), or other suitable material that is ductile and exhibits non-elastic deformation similar to metals.

In another aspect, the present inventions feature methods of forming a fluidic connection between two fluidic conduits. The methods operate on a tubing assembly comprised of an outer tube having disposed within a first inner tube and a second inner tube where the first inner tube is affixed to the outer tube, and where a support tube is disposed in the second inner tube. Various embodiments of the methods of forming a fluidic connection between two fluidic conduits can operate on a tubing assembly comprised of a fragile tube, such as for example silica capillary tubes and the like, predisposed (i.e. present within an inner tube before the fluidic connection is formed) within the first and/or second inner tube.

In one aspect of the methods of the present inventions, an outer tube is provided having disposed therein a first inner tube and a second inner tube, where the first inner tube is affixed to the outer tube, and where a support tube is disposed in the lumen of the second inner tube. The second inner tube is abutted against the first inner tube. For the sake of more exact expression, the first inner tube and second inner tubes both have first and second ends and the second end of the second inner tube is abutted against the first end of the first inner tube. The area of contact between the second end of the second inner tube and the first end of the first inner tube defines an end interface.

In various embodiments, the first inner tube is affixed to the outer tube by heating such that the outer surface of the first inner tube softens or partially melts and adheres upon cooling to the inner surface of the outer tube. In various embodiments of affixing the first inner tube to the outer tube by heating an intermediate tube, or sleeve, is disposed about the first inner tube and the application of heat cause the intermediate tube to shrink, soften, and/or melt and upon cooling the intermediate tube adheres to the outer surface of the first inner tube and the inner surface of the outer tube, thereby affixing the first inner tube to the outer tube. In various embodiments, the first inner tube is affixed to the outer tube by deforming the outer tube to create a radial crimp at a longitudinal location between the end interface and the second end of the first inner tube.

A distance x, in a longitudinal direction away from the end interface towards the first end of the second inner tube, is selected for formation of a first radial crimp. The distance x is selected such that upon formation of the first radial crimp (e.g. by circumferential deformation of the outer tube) the material of the second inner tube is extruded in a longitudinal direction from the location of the first radial crimp towards the end interface to create a fluid-tight seal between the second end of the second inner tube and the first end of the first inner tube at the end interface. In various preferred embodiments, the distance x is selected such that upon deformation of the outer tube a stress of between about 70 MPa to about 200 MPa, and preferably between about 100 MPa and about 150 MPa, is applied against the first end of the first inner tube by extrusion of the second inner tube in the longitudinal direction towards the end interface.

After selection, the outer tube is deformed to create the first radial crimp at the distance x from the end interface, and then in various embodiments the outer tube is deformed to create a second radial crimp at a longitudinal location in the direction of the first radial crimp and further away from the end interface than the first radial crimp, preferably at a location a distance about twice x from the end interface, and in various embodiments between the end interface and the first end of the second inner tube. In various embodiments, the second radial crimp serves to further hold the second inner tube motionless within the outer tube. In various embodiments, the second radial crimp provides a fluidic seal between the outer surface of the second inner tube and the inner surface of the outer tube; however, it is to be understood that the second radial crimp is not required to provide a fluidic seal as a fluidic seal is formed over at least a portion of the end interface between the first end of the first inner tube and the second end of the second inner tube. In addition, in various embodiments, the first radial crimp also forms a radial fluidic seal between the inner surface of the second inner tube and the outer surface of the support tube.

In another aspect, the invention features a method of forming a chromatographic column assembly. In various embodiments, an outer tube is provided having disposed therein a first inner tube and a second inner tube, where the first inner tube is affixed to the outer tube, and where a support tube is disposed in the lumen of the second inner tube. The first inner tube can be affixed to the outer tube in many ways as described herein. Within the lumen of the first inner tube, the support tube, or both, is disposed a chromatographic media.

In various embodiments, a chromatographic column assembly is formed comprising one or more additional inner tubes containing a chromatographic media. These one or more additional inner tubes are predisposed within lumen of the first inner tube or support tube, that is, disposed within the inner or support tube prior to the step of deforming the outer tube.

The second inner tube is abutted against the first inner tube. The first inner tube and second inner tubes both have first and second ends and the second end of the second inner tube is abutted against the first end of the first inner tube. The area of contact between the second end of the second inner tube and the first end of the first inner tube defines an end interface.

A distance x, in a longitudinal direction away from the end interface towards the first end of the second inner tube, is selected for formation of a first radial crimp. The distance x is selected such that upon formation of the first radial crimp (e.g. by circumferential deformation of the outer tube) the material of the second inner tube is extruded in a longitudinal direction from the location of the first radial crimp towards the end interface to create a fluid-tight seal between the second end of the second inner tube and the first end of the first inner tube at the end interface. The greater fluidic pressure the seal is projected to withstand, the shorter the distance x from the range of distances should be selected. However, it is to be understood, according to the present inventions, that too short of a distance x will not provide enhanced sealing but rather could result in unacceptable deformation of the second inner tube in the radial direction, and thus exert stress (radial compression) sufficient to crack a silica tube in the lumen of the second inner tube and/or the first inner tube. Accordingly, the inventors have discovered a range wherein sufficient sealing can be made to occur without undue radial deformation or imposition of undue stress on tubes near the sealing region.

After selection, the outer tube is deformed to create the first radial crimp at the distance x from the end interface, and then in various embodiments the outer tube is deformed to create a second radial crimp at a longitudinal location in the direction of the first radial crimp and further away from the end interface than the first radial crimp, preferably at a location a distance about twice x from the end interface, and in various embodiments between the end interface and the first end of the second inner tube. In various embodiments, the second radial crimp serves to further hold the second inner tube motionless within the outer tube. In various embodiments, the second radial crimp provides a fluidic seal between the outer surface of the second inner tube and the inner surface of the outer tube; however, it is to be understood that the second radial crimp is not required to provide a fluidic seal as a fluidic seal is formed over at least a portion of the end interface between the first end of the first inner tube and the second end of the second inner tube. In addition, in various embodiments, the first radial crimp also forms a radial fluidic seal between the inner surface of the second inner tube and the outer surface of the support tube.

In various embodiments, a chromatography column assembly is made comprising a both a third inner tube predisposed in the lumen of the first inner tube and a fourth inner tube predisposed in the lumen of the support tube where a chromatographic media or sorbent bed is disposed in the lumens of the third and fourth inner tubes.

In various embodiments of methods of the present inventions, a length $L_{C1}$ for the first radial crimp is also selected. However, it is to be understood that precision is not necessarily required in selecting the first radial crimp length $L_{C1}$ nor in forming the first radial crimp to that length. Moreover, it is to be understood that in the context of selecting a radial crimp length such selection can be met by choice of tool to make the radial crimp. In various embodiments, knowledge of the first radial crimp length is used to ensure that the support tube extends at least from the first end of the first tube and past the first radial crimp. In various embodiments, the support tube extends past the first end of the first tube and into the lumen of the first inner tube. In various preferred embodiments, the support tube extends past the second radial crimp.

The support tube of in the present methods can be of a variety of materials and is selected to be comprised of a material more resistant to radial compression than the material of the second inner tube, such that, for example, upon formation of the first radial crimp the support tube substantially limits deformation of the second inner tube in a radially inward direction in the region about the first radial crimp. In various embodiments, the support tube is comprised of a material having a Young's modulus that is greater than the Young's modulus of the material comprising the second inner tube.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the inventions.

DETAILED DESCRIPTION

Figure 1A:
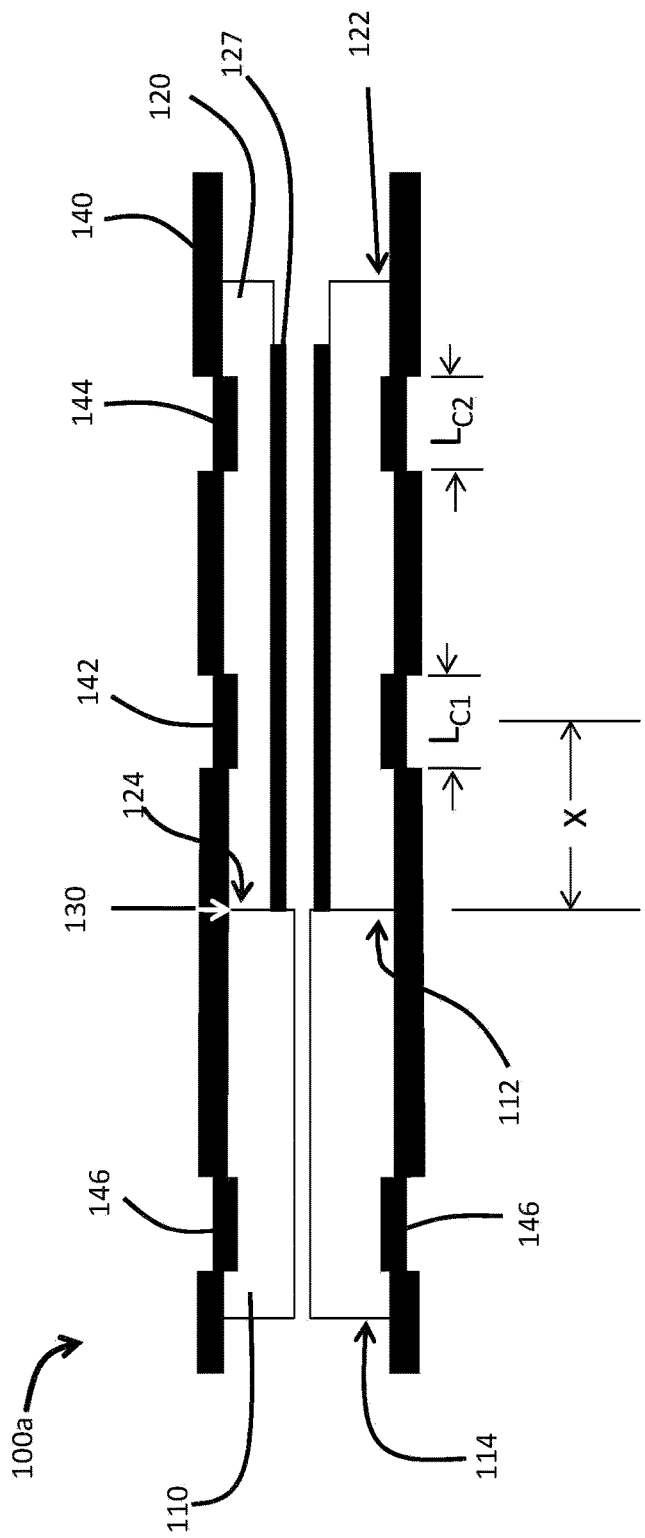
FIGS. 1A-1F are schematic cross-sectional illustrations of a tubing assembly according to various aspects and embodiments of the inventions.
Figure 1B:
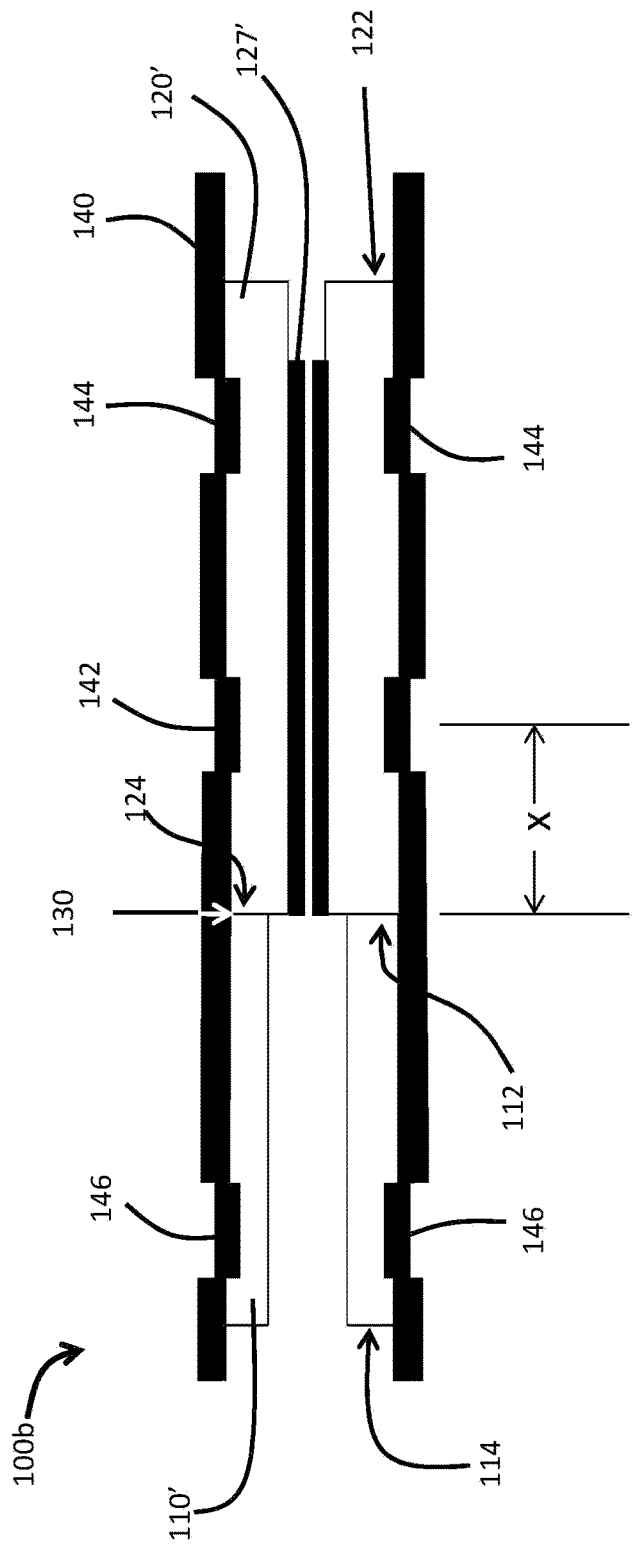
Figure 1C:
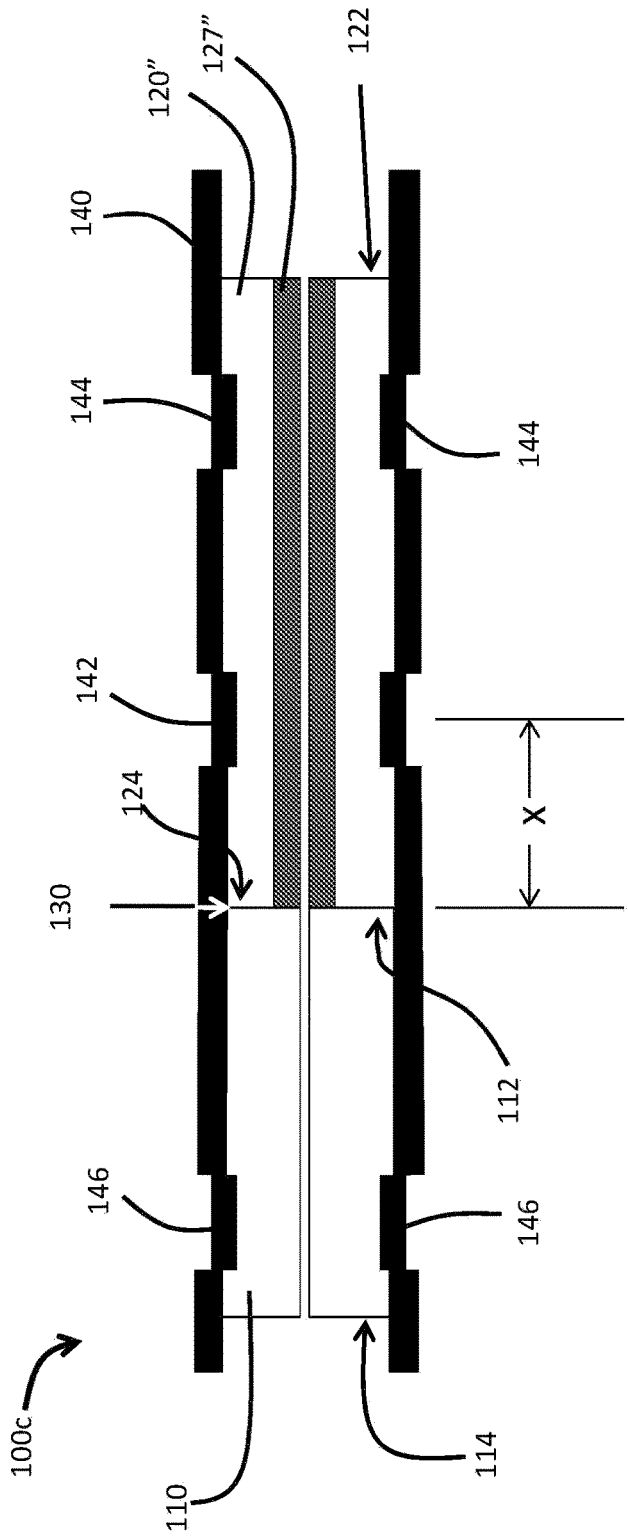
Figure 1D:
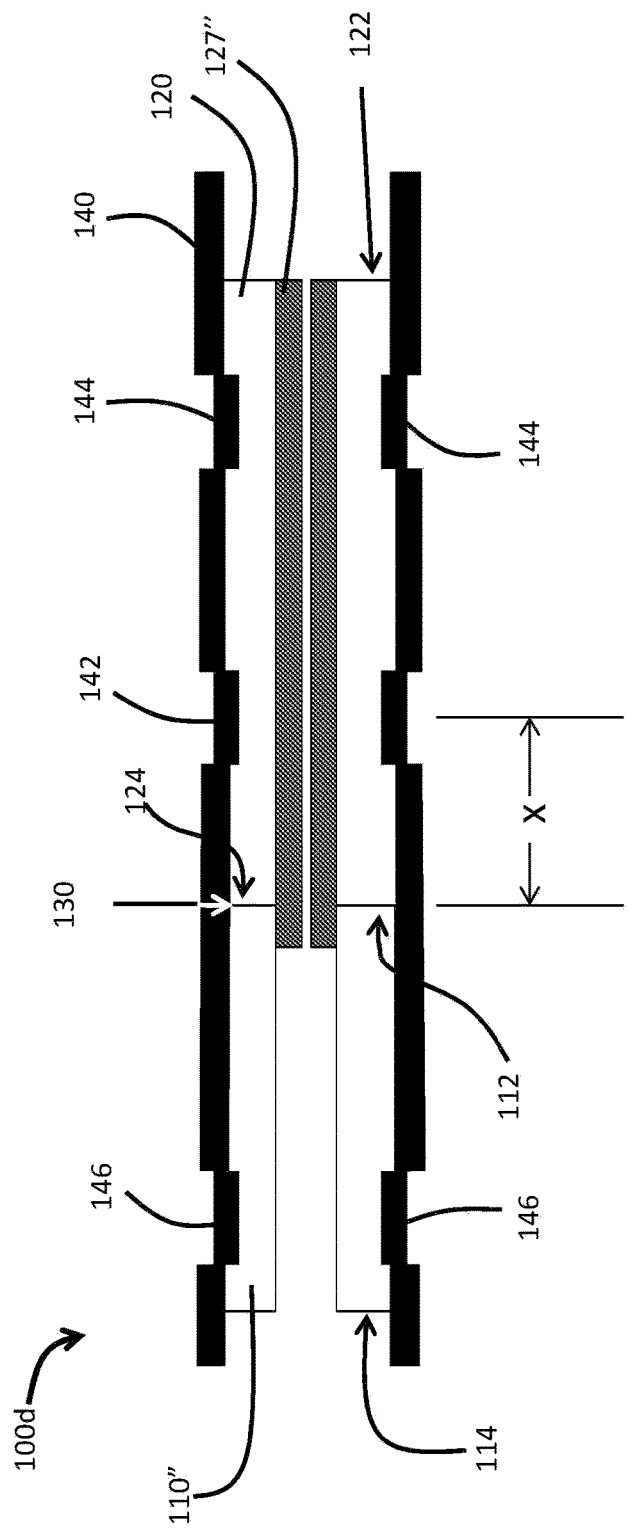

Reference in the specification to "one embodiment," "an embodiment," "one aspect," or "an aspect" means that a particular, feature, structure or characteristic described in connection with the embodiment or aspect is included in at least one embodiment or aspect of the teachings. References to a particular embodiment or aspect within the specification do not necessarily all refer to the same embodiment or same aspect.

It is to be understood that as used herein and in the claims the terms "first", "second", "third" and "fourth" with respect, for example, to inner tubes and crimps are used merely to distinguish the elements and that the use of these ordinal references is not meant to be limiting as to the order in which elements or crimps are introduced or to imply the total number of inner tube elements in an embodiment. For example, various embodiments of the inventions exist that include a first inner tube, a second inner tube and a fourth inner tube but that do not include a third inner tube. Further, for example, in various embodiments a third radial crimp is made before a first radial crimp.

As used herein, when the terms "affixed" or "affixing," when used to describe the relation between an inner tube and outer tube includes any assembly that holds the inner tube substantially motionless within the outer tube with respect to longitudinal motion. For example with respect to the first inner tube, holding the first inner tube substantially motionless within the outer tube with respect to longitudinal motion during the process that forms the first radial crimp. Accordingly, it is to be understood that various embodiments of the present invention do not require that the first inner tube be permanently combined with the outer tube. Examples of an assembly that can affix the first inner tube to the outer tube include, but are not limited to, a nut, fitting, block, ring, ferrule or other structure that substantially prevents the first inner tube from moving in a longitudinal direction away from the end interface.

Further examples of an assembly that can affix an inner tube to the outer tube include, but are not limited to, glue, epoxy, resin, etc., between the outside of the first inner tube and inside of the outer tube. Other examples of an assembly that can affix an inner tube to the outer tube include, but are not limited to, softening or partially melting the inner tube to provide an assembly that affixes it to the outer tube, for example, the first inner tube is in various embodiments is affixed to the outer tube by heating such that the outer surface of the first inner tube softens or partially melts and adheres upon cooling to the inner surface of the outer tube. In various examples, an intermediate tube is used to affix an inner tube to the outer tube, in various embodiments, an intermediate tube, or sleeve, is disposed about the first inner tube and the application of heat causes the intermediate tube to shrink, soften, and/or melt and upon cooling the intermediate tube adheres to the outer surface of the inner tube and the inner surface of the outer tube, thereby affixing the inner tube to the outer tube.

Other examples of an assembly to affix an inner tube to the outer tube include radial crimps, for example, in various embodiments; the first inner tube is affixed to the outer tube by deforming the outer tube to create a radial crimp at a longitudinal location between the end interface and the second end of the first inner tube. It is to be understood that a radial crimp used to affix the first inner tube to the outer tube is not itself required to provide a fluidic seal as a fluidic seal is formed over at least a portion of the end interface between the first end of the first inner tube and the second end of the second inner tube.

As used herein, the term "sorbent bed" is used broadly to refer to filtration media and well as chromatographic media. For example, in various embodiments a sorbent bed permanently removes a contaminant in a fluid stream, such as, e.g., particulates and/or dissolved impurities. In various embodiments, the sorbent bed comprises a chromatographic media such as, for example, silica particles. As used herein, "chromatographic media" refers to any stationary phase media that can be used to perform a chromatographic process, including, but not limited to, sample-preparation and analytical chromatography, as in such methods as size exclusion, ion exchange, reverse phase, affinity chromatography and the like.

In various embodiments, the assemblies further include a coupling body to fluidically couple an assembly of the present inventions to a fluidic system. As used herein, a coupling body means a body that has a bore to receive a tube assembly and a fluid channel to receive a fluid from or provide a fluid to the tube assembly. By way of example, an injector valve or a chromatography column for a liquid chromatography system may include a coupling body to couple fluid to or from a tube assembly of the present inventions to another component of the liquid chromatography system.

In brief overview, the invention relates to tubing assemblies, including assemblies comprising chromatographic columns, and methods for forming a fluidic connection to make the same. The assemblies include an outer tube having disposed therein a first inner tube and a second inner tube, the second inner tube having disposed therein a support tube. Prior to formation of a fluidic connection the first inner tube is affixed to the outer tube. The second inner tube is formed of a polymeric material and the outer tube of a metal or a ductile material that exhibits non-elastic deformation like a metal. The support tube is formed of a material more resistant to deformation by radial compression than the second inner tube. The second inner tube is abutted against the first inner tube, where the tubes abut is referred to herein as the end interface. A radial crimp is made in the outer tube over the second inner tube a distance x from the end interface. This radial crimp extrudes a portion of the second inner tube in the direction towards the end interface. The support tube limits and/or substantially prevents the first radial crimp from collapsing or narrowing the lumen of the second inner tube about the region of the first radial crimp and, in various embodiments, assists in directing the second inner tube deformation in a longitudinal direction. In addition, in preferred embodiments, the first radial crimp also forms a radial fluidic seal between one or more of: (a) the inner surface of the second inner tube and the outer surface of the support tube; (b) the inner surface of the outer tube and the outer surface of the second inner tube; and (c) between the contacting surfaces of all tubes within the lumen of the outer tube at the location of the first radial crimp.

Through proper selection of the distance x, as taught herein, the extruded portion of the second inner tube is deformed against the end of the first inner tube forming a seal able to withstand high fluidic pressure (e.g., greater than an about 70 MPa, approximately about 10,000 psi), sufficient for use, e.g., in HPLC and UPLC® chromatographic applications. The seal so formed is integral with the tube assembly, thus problems associated with handling small dimension conduits are reduced or avoided and dead and unswept volumes at the fluidic coupling are reduced or eliminated. In addition, through proper selection of the distance x, as taught herein, chromatographic column assemblies comprising, e.g., a capillary tube predisposed within the first or second inner tube prior to formation of the seal can be made as radial compressive forces which can deform (e.g., crack) a capillary tube are relieved by a suitable distance x that the second inner tube to deform in the longitudinal sufficient to relieve the stress in the radial direction yet form a face seal against the first end of the first inner tube.

The present teachings will now be described in more detail with reference to embodiments thereof as shown in the accompanying drawings. While the present teachings are described in conjunction with various embodiments and examples, it is not intended that the present teachings be limited to such embodiments. On the contrary, the present teachings encompass various alternatives, modifications and equivalents, as will be appreciated by those of skill in the art.

Those of ordinary skill having access to the teachings herein will recognize additional implementations, modifications and embodiments, as well as other fields of use, which are within the scope of the present disclosure.

It is to be understood that the teachings, discussion and disclosures herein with respect to, for example, the inner tubes, outer tube, radial crimps, materials, dimensions, distance x, crimp depth, crimp length, etc. with respect to one set of figures apply as well to other sets of figures, and such teachings, discussions and disclosures are not repeated with respect to discussion of each set of figures and embodiments for the sake enhanced clarity.

It is to be understood that although the crimp depths $\Delta_1$ and $\Delta_2$ are and the crimp lengths $L_{C1}$ and $L_{C2}$ are schematically illustrated in FIGS. 1A-1F, 2A-2D, 3A-3C and 4 as roughly equal, this is not a requirement and these crimp depths and lengths can differ. In addition, although the crimps in FIGS. 1A-1F, 2A-2D, 3A-3C and 4 are schematically illustrated as a near step-like change in diameter of the outer surface of the outer tube, in other embodiments the cross-sectional shape of the crimps may include a more gradual slope for the diameter transition at the crimp edges. In addition, the "bottom" of the crimps may not be as flat as shown in the figures.

FIGS. 1A to 1D show a cross-sectional view of a tubing assembly 100a, 100b, 100c, 100d according to various aspects and embodiments of the present inventions. The tubing assembly comprises a first inner tube 110, 110', 110" and a second inner tube 120,120', 120" both disposed within an outer tube 140, and a support tube 127, 127', 127" disposed within the second inner tube 120, 120', 120". The first inner tube having a first end 112 and a second end 114 and the second inner tube having a first end 122 and a second end 124. The first end 112 of the first inner tube abuts against the second end 124 of the second inner tube. The area of contact between the second end 124 and the first end 112 defines an end interface 130. It is to be understood that the inner diameters of the first inner tube and second inner tube can be the same (FIG. 1D) or different and that in various embodiments the first inner tube has a smaller inner diameter than the second inner tube (see, e.g., FIGS. 1A, 1C) and in others the first inner tube has a larger inner diameter than the second inner tube (see, e.g., FIGS. 1B, 1D). It is to be understood that the outer diameters of the first and second inner tubes are selected to fit within the outer tube, and the outer diameter of the support tube is selected to fit within the second inner tube.

It is to be understood that the inner diameters of the first inner tube, second inner tube and support tube can be the same or different and that the support tube can extend past the end interface 130 into the lumen of the first inner tube (or the lumen of a another inner tube disposed within the first inner tube if a third inner tube is present); however, it is not required that the support tube extend into the first inner tube when the inner diameters of the first and second inner tubes are the same. In various embodiments where the support tube does not extend into the lumen of the first inner tube, it is preferred that an end of the support tube is substantially coplanar with the end interface.

In various embodiments, the outer tube 140 has at least two radial crimps, a first radial crimp 142 and a second radial crimp 144. The first radial crimp 142 is at a longitudinal location along the outer tube in a direction away from the end interface 130 towards the first end 122 of the second inner tube 120, 120', 120" at a distance x from the end interface and the second radial crimp 144 is at a longitudinal location along the outer tube in the direction of the first radial crimp and further away from the end interface than the first radial crimp. In various embodiments the second radial crimp 144 is located at a longitudinal location along the outer tube between the first radial crimp 142 and the first end 122 of the second tube. The distance x is such that deformation of the outer tube 140 to create the first radial crimp 142 forms a fluid-tight seal between the second end 124 of the second inner tube and the first end 112 of the first inner tube at the end interface 130.

It is to be understood that the length of the support tube and the placement of the support tube are selected such that the support tube extends at least from the first end of the first inner tube towards and past the first radial crimp. In various embodiments, the support tube extends into the lumen of the first inner tube (see, for example one embodiment illustrated in FIG. 1D. In preferred embodiments, the support tube extends at least from the first end of the first inner tube towards and past the second radial crimp.

In the present inventions, the joining of the first inner tube to the second inner tube at the end interface substantially eliminates dead volume at the seal and thus reduces unswept volume for liquids flowing through the assembly. Accordingly, assemblies of the present inventions, e.g., 100a, 100b, 100c, 100d, 101, 101', 200, 201, 201', 300, 301, 302, 400 can be used as components of a liquid chromatography system, to reduce dead volumes and carryover that can adversely affect chromatographic measurements.

Without being held to theory, in various embodiments the distance x is a distance at which the stress applied by the second end of the second inner tube against the end interface is between about between about 70 MPa to about 200 MPa, and preferably between about 100 MPa and about 150 MPa. Without being held to theory, the stress applied against the end interface is related to the distance x, the circumferential stress created by the first crimp, 142, 242, 342 and the Young's modulus of the second inner tube. The circumferential stress applied by the first crimp is in turn determined primarily by the first radial crimp depth ($\Delta_1$) and first radial crimp length ($L_{C1}$). For example, in various embodiments where, for example, the second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 711 micrometers (28 thousandths of an inch, 0.028"), with a first crimp of depth between about 0.003 inches and about 0.01 inches, and a first crimp length between about 0.05 inches and about 0.125 inches, the distance x is between about 3.6 millimeters to about 28 millimeters (in U.S. English units between about 0.14 to about 1.1 inches), and preferably x is about 5 millimeters (about 0.20 inches) with a crimp depth of about 0.15 mm (0.006 inches) and a crimp length of about 1.58 mm (0.062 inches).

In various preferred embodiments, to produce a fluidic face seal at the end interface sufficient to withstand an operating fluidic pressure greater than about 15,000 psi (about 100 MPa), and preferably less than about 22,000 psi, the distance x is chosen to result in a sealing stress at the end interface of between about one (1×) and about two (2×) times the operating fluidic pressure (referred to as a gasket factor), and preferably about one and a half times (1.5×) the operating fluidic pressure.

Without being held to theory, the distance x according to the present inventions is directly proportional to the volume displaced by the first radial crimp and inversely proportional to the end interface stress (sealing pressure) desired. For example, as the volume displaced increases the distance x is increased to maintain a sealing stress at the end interface of between about one (1×) and about two (2×) times the operating fluidic pressure, and preferably about one and a half times (1.5×) the operating fluidic pressure. Without being held to theory, the percentage change in volume results in the stress produced at the end interface. In various embodiments, the volumetric change (i.e. volume displaced by the first radial crimp) is between about 2.9% and 5.7%, and preferably about 4.2% to produce, respectively a sealing stress at the end interface of between about one (1×) and about two (2×) times the operating fluidic pressure, and preferably about one and a half times (1.5×) the operating fluidic pressure.

Adjustment of the distance x shall now be illustrated by way of the following non-limiting examples. It is to be understood that although the following examples are discussed in the context of a first radial crimp and second inner tube, they can be applied equally well to the embodiments including multiple face seals; for example, determination of $x_a$ and/or $x_b$ in FIG. 4, where a sealing tube is equated to the second inner tube and a sealing radial crimp is equated to the first radial crimp.

Example 1: The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 711 micrometers (28 thousandths of an inch, 0.028"), with a first crimp of depth about 0.006 inches, and a first crimp length of about 0.062 inches, the preferred distance x, is about 8.6 millimeters (about 0.34 inches).

Example 2: The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 381 micrometers (15 thousandths of an inch, 0.015"), with a first crimp of depth about 0.006 inches, and a first crimp length of about 0.062 inches, the preferred distance x, is about 7.3 millimeters (about 0.29 inches).

Example 3: The second inner tube is a polyethylene terephthalate (PET) polymeric tube with a Young's modulus (aka modulus of elasticity) of about 2.8 GPa, an outer diameter of about 1575 micrometers (62 thousandths of an inch, 0.062") and an inner diameter of about 711 micrometers (28 thousandths of an inch, 0.028"), with a first crimp of depth about 0.007 inches, and a first crimp length of about 0.062 inches, the preferred distance x, is about 7.9 millimeters (about 0.31 inches).

Example 4: The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 711 micrometers (28 thousandths of an inch, 0.028"), with a first crimp of depth about 0.01 inches, and a first crimp length of about 0.062 inches, the preferred distance x, is about 13.7 millimeters (about 0.54 inches).

Example 5: The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 711 micrometers (28 thousandths of an inch, 0.028), with a first crimp of depth about 0.01 inches, and a first crimp length of about 0.1 inches, the preferred distance x, is about 22 millimeters (about 0.97 inches).

In various embodiments, the outer tube is a stainless steel tube with outer diameter of about 2108 micrometers (83 thousandths of an inch, 0.083") and an inner diameter of about 1600 micrometers (63 thousandths of an inch, 0.063"); the second inner tube is a polyether ether ketone (PEEK) polymeric tube with outer diameter of about 1575 micrometers (62 thousandths of an inch, 0.062") and an inner diameter of about 711 micrometers (28 thousandths of an inch, 0.028"); and the support tube is a fused silica capillary tube with outer diameter of about 686 micrometers (27 thousandths of an inch, 0.027") and an inner diameter of about 305 micrometers (12 thousandths of an inch, 0.012").

In various embodiments, the outer tube is a stainless steel tube with outer diameter of about 2108 micrometers (83 thousandths of an inch, 0.083") and an inner diameter of about 1600 micrometers (63 thousandths of an inch, 0.063"); the second inner tube is a polyether ether ketone (PEEK) polymeric tube with outer diameter of about 1575 micrometers (62 thousandths of an inch, 0.062") and an inner diameter of about 381 micrometers (15 thousandths of an inch, 0.015"); and the support tube is a fused silica capillary tube with outer diameter of about 381 micrometers (15 thousandths of an inch, 0.015") and an inner diameter of about 76 micrometers (3 thousandths of an inch, 0.003").

In various embodiments, the second radial crimp 144, 244, 344 is positioned a distance about twice the distance x from the end interface at a longitudinal location along the outer tube away from the end interface in the direction of the first end of the second tube. In various embodiments, the second radial crimp forms a radial fluidic seal between one or more of: (a) the inner surface of the second inner tube and the outer surface of the support tube; (b) the inner surface of the outer tube and the outer surface of the second inner tube; and (c) between the contacting surfaces of all tubes within the lumen of the outer tube at the location of the second radial crimp.

In the present inventions, the second inner tube is made of a polymeric material, the outer tube is made of a metal (e.g., a stainless steel), or other suitable material that is ductile and exhibits non-elastic deformation similar to metals, and the first inner tube can be made from a variety of materials, including, but not limited to a metal, such as stainless steel, or a polymeric material. A wide range of polymeric materials are suitable for use as the second inner tube material and are preferably chosen based on the Young's modulus of the material and chemical compatibility with the operating fluid.

In various embodiments, the polymeric material of the second inner tube has a Young's modulus in the range between about 0.4 to about 5 gigapascals (GPa). In various embodiments the polymeric material has a Young's modulus in the range between about 0.4 to about 1 GPa such as, for example, polytetrafluoroethylene (PTFE) polymers, high density polyethylene (HDPE) polymers and the like. In various embodiments the polymeric material has a Young's modulus in the range between about 1 to about 2 GPa such as, for example, polypropylene (PP) polymers and the like. In various embodiments the polymeric material has a Young's modulus in the range between about 2 to about 3 GPa such as, for example, polyethylene terephthalate (PET) polymers and the like. In various embodiments the polymeric material has a Young's modulus in the range between about 3 to about 4 GPa such as, for example, polyether ether ketone (PEEK) polymers and the like. In various embodiments the polymeric material has a Young's modulus in the range between about 4 to about 5 GPa such as, for example, polyaryletherketone (PAEK) polymers and the like.

The support tube can be made of a variety of materials provided that they are more resistant to deformation due to compression than the second inner tube. In various embodiments, the support tube is comprised of one or more of a ceramic, a glass or metal. A preferred glass for the support tube material is a fused silica glass and a preferred metal for the support tube is a stainless steel.

Referring to FIGS. 1A-1F, in various embodiments, the outer tube 140 employs a third radial crimp 146 to affix the first inner tube to the outer tube. It is to be understood that other means can be employed to affix the first inner tube to the outer tube, including, but not limited to, mechanical means (such as, e.g., a nut, fitting, block, ring, ferrule), chemical means (such as, e.g., epoxy, resin, glue), alteration means (such as, e.g., softening or partially melting the first inner tube to the outer tube or an intermediate tube to the outer surface of the first inner tube and the inner surface of the outer tube), or other means that substantially prevents the first inner tube from moving in a longitudinal direction away from the end interface. Although a third radial crimp is illustrated in FIGS. 1A-1E, 2A-2D, and 3A-C, it is thus to be understood that a third radial crimp 146, 246, 346 is not necessary to practice the present inventions, rather many means can be employed to affix the first inner tube to the outer tube prior to or during formation of the first radial crimp 142, 242, 342.

Figure 1E:
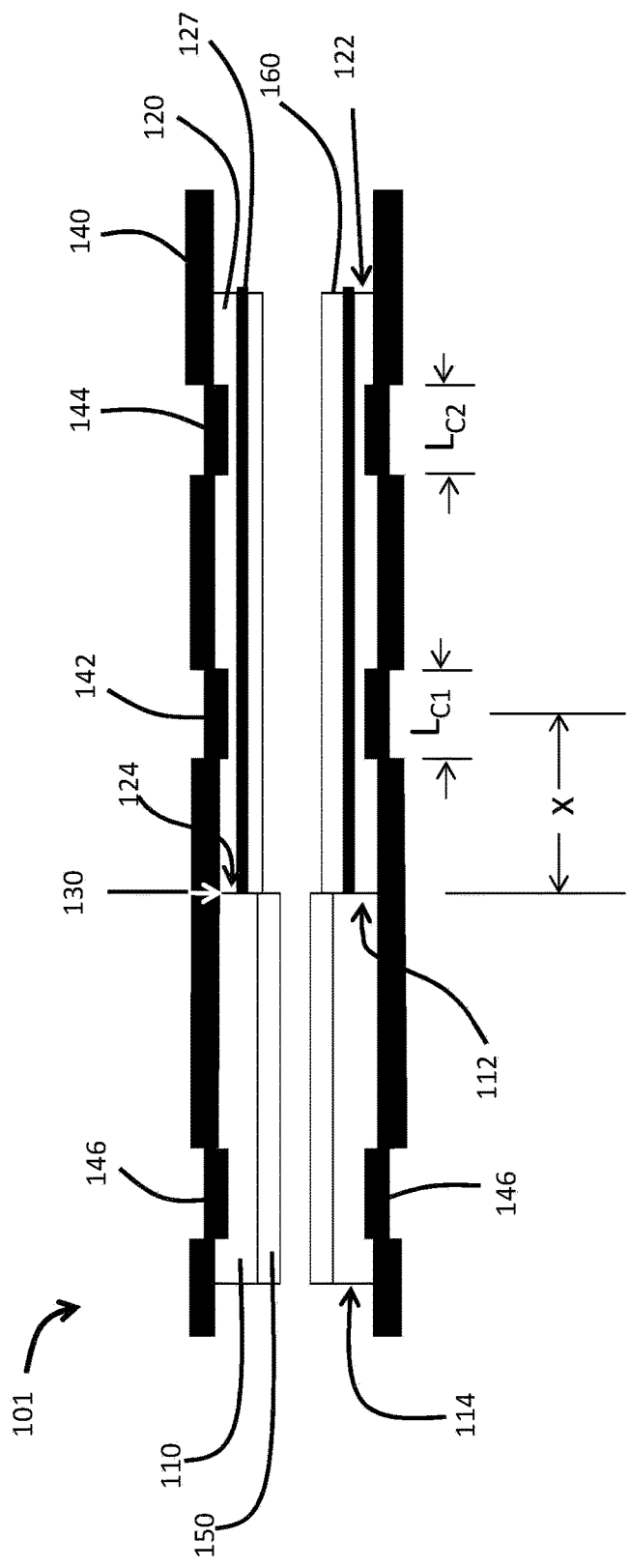
Figure 1F:
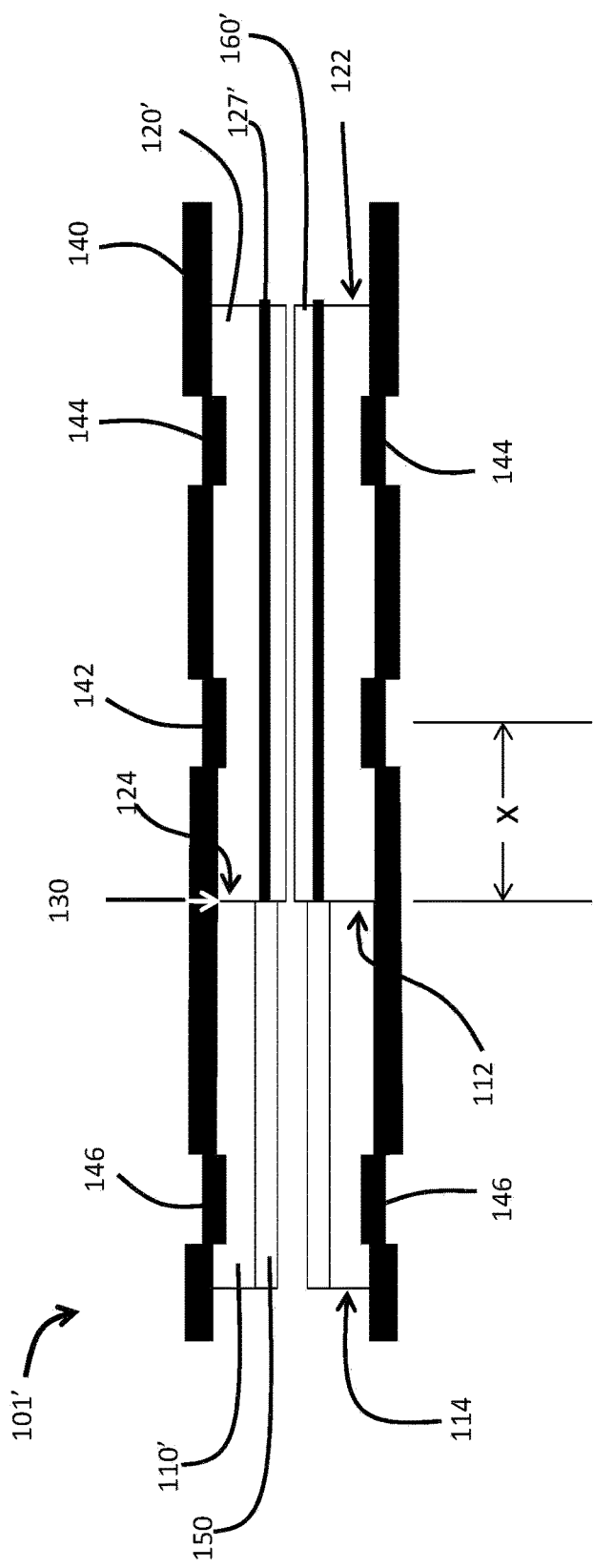
Figure 2A:
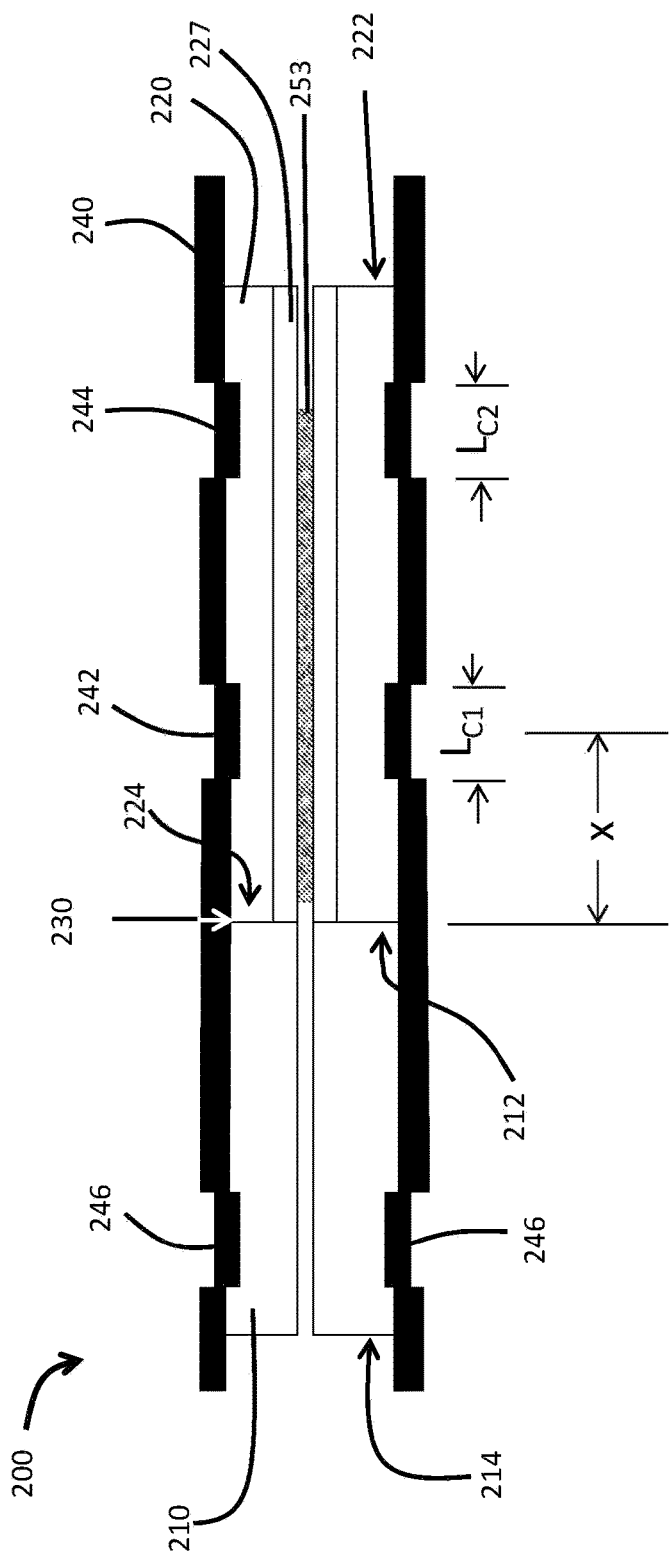
FIGS. 2A-2D are schematic cross-sectional illustrations of a chromatographic column assembly according to various embodiments of the inventions.
Figure 2B:
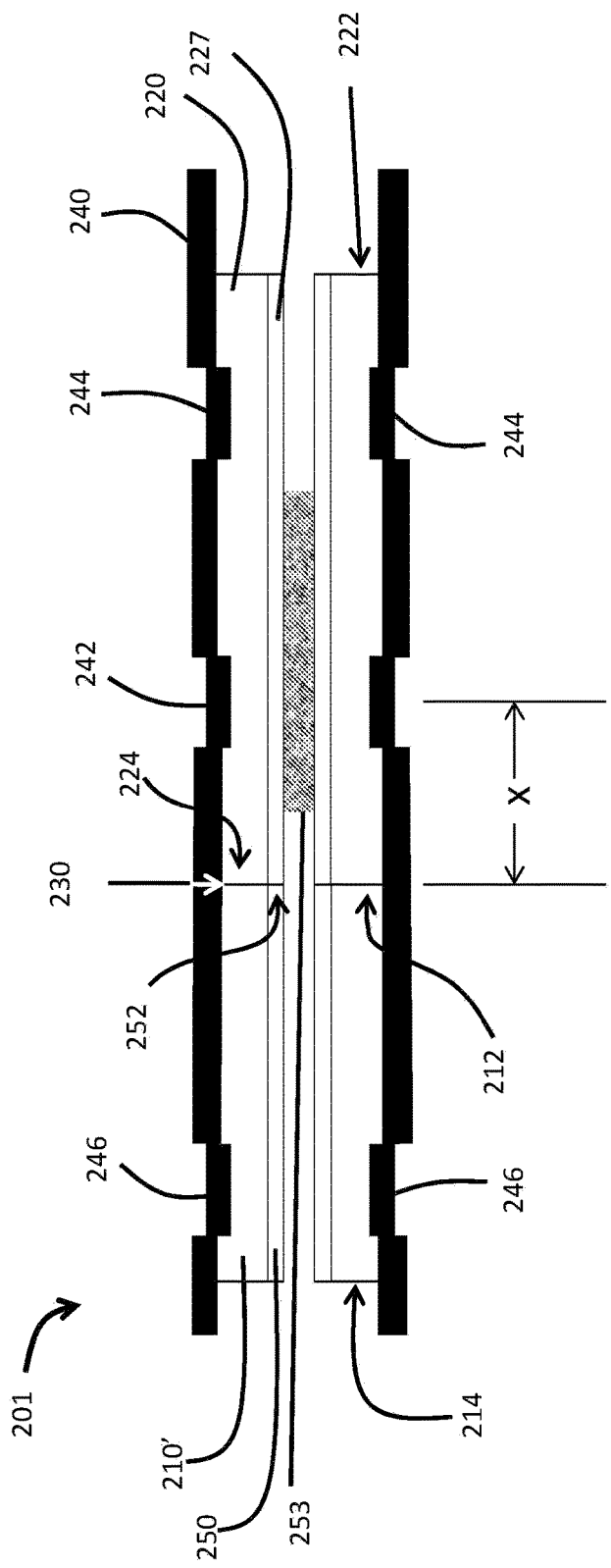
Figure 2C:
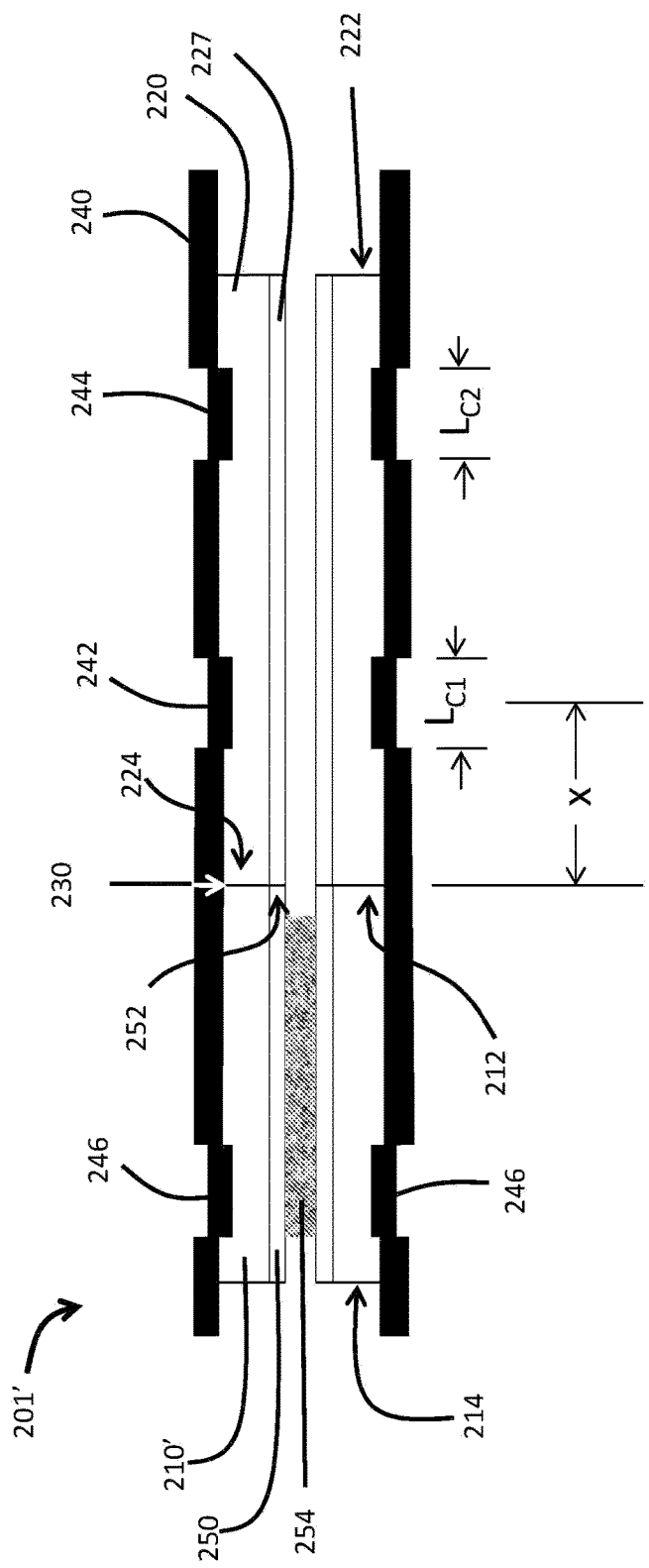
Figure 2D:
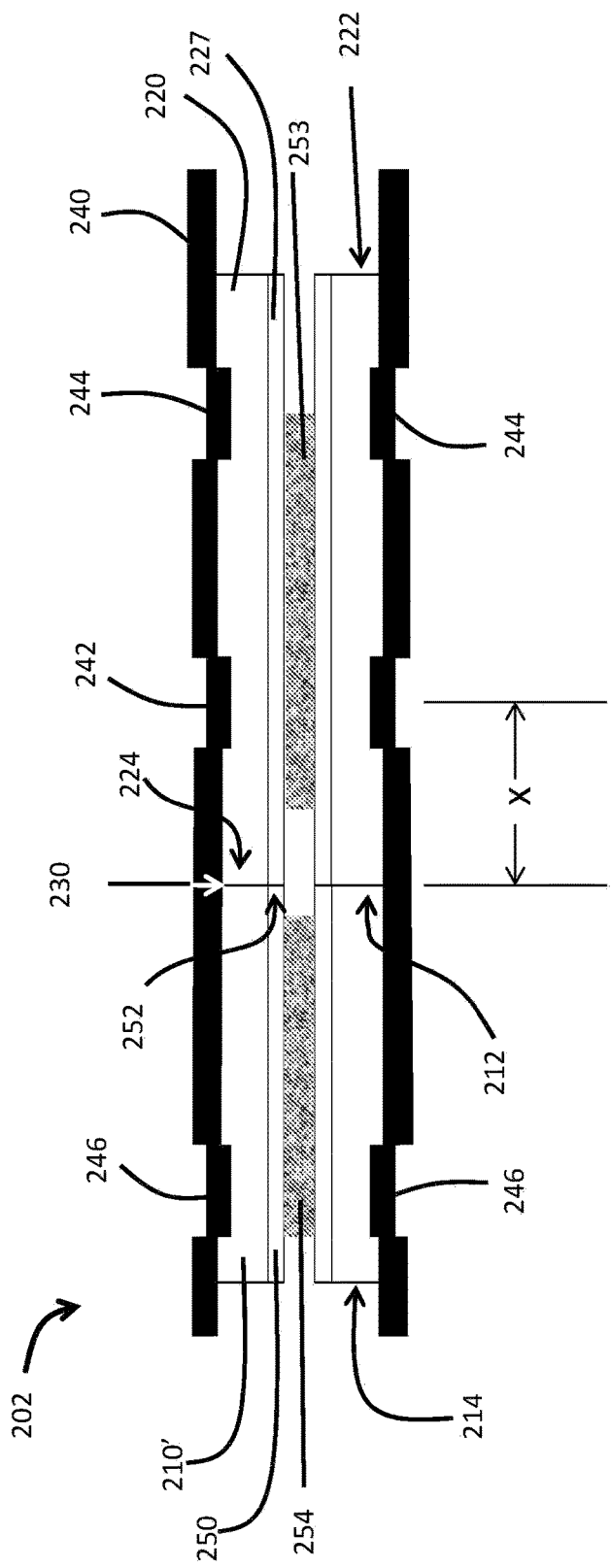

In various embodiments, additional tubes and/or material are disposed within the lumens of the first inner tube, second inner tube, or both. Referring to FIGS. 1E-1F, in various embodiments the tubing assembly 101, 101' includes a third inner tube 150 disposed within the lumen of the first inner tube 110 and a fourth inner tube 160, 160' disposed within the lumen of the support tube 127, 127'. It is to be understood that although FIGS. 1E and 1F illustrate additional tubes within the lumens of both the first inner tube and support tube, embodiments using only a third or only a fourth inner tube are also embodiments within the present inventions.

The third and fourth inner tubes can be made of a wide range of materials as the fluidic seal is achieved between the ends of the first and second inner tubes, and in various embodiments a radial fluidic seal is achieved between the inner surface of the second inner tube and the outer surface of the support tube by the first radial crimp. In addition, in various aspects the proper selection of the distance x in the formation of the tubing assembly allows for use of fragile first, third and fourth inner tubes, such as, e.g. silica glass capillary tubes, because the distance x is long enough for longitudinal extension of the second inner tube to decrease the radial compression on the first, third and/or fourth inner tubes yet the distance x is short enough to make a fluid-tight seal against the first end of the first inner tube.

Referring to FIGS. 2A-2D, in various aspects also provided are chromatographic column assemblies. In various embodiments a chromatographic column assembly 200, 201 201', 202 comprises a first inner tube 210, 210', a second inner tube 220 both disposed within an outer tube 240 and a support tube 227 disposed within the lumen of the second inner tube. The support tube 227 extends at least from the first end 212 of the first tube and past the first radial crimp 242. In various embodiments, the support tube extends past the first end of the first tube and into the lumen of the first inner tube. In various preferred embodiments, the support tube extends past the second radial crimp 244. In various embodiments where the support tube does not extend into the lumen of the first inner tube, it is preferred that an end of the support tube is substantially coplanar with the end interface 230.

In various embodiments, a third inner tube 250 is disposed in the lumen of the first inner tube, or a fourth inner tube (not illustrated) is disposed in the lumen of the support tube, or both. The first end 212 of the first inner tube 210, 210' abuts against the second end 224 of the second inner tube 220. The area of contact between the second end 224 and the first end 212 defines an end interface 230. In embodiments comprising a third inner tube 250, it is preferred that the first end 252 of the third inner tube is substantially coplanar with the first end 212 of the first inner tube; in embodiments comprising a fourth inner tube (not illustrated), it is preferred that the second end of the fourth inner tube (the end nearest the end interface) is substantially coplanar with the second end 224 of the second inner tube; and in embodiments comprising both a third and fourth inner tube it is preferred that the first end 252 of the third inner tube abuts the second end of the fourth inner tube at a plane substantially coplanar with the end interface 230.

The chromatographic column assemblies also comprise one or more sorbent beds. A sorbent bed is disposed in the support tube, a third inner tube, a fourth inner tube, or both. Referring to FIGS. 2A-2D, in various embodiments a sorbent bed 253 is disposed in the lumen of the support tube 227 (see, e.g., FIGS. 2A, 2B), a sorbent bed 254 is disposed in the lumen of the third inner tube 250 (see, e.g., FIG. 2C), or sorbent beds 253, 254 are disposed in both the third inner tube 250 and the support tube 227 (see, e.g., FIG. 2D).

The sorbent bed in the present inventions can be of a variety of materials, such as, for example, those used for filtration, ion exchange, affinity chromatography, chromatographic separation, and the like. For example, in various embodiments the sorbent bed serves as a sample-preparation chromatography column or an analytical chromatography column. In various preferred embodiments comprising a sorbent bed in a third inner tube and a sorbent bed in a fourth inner tube, one sorbent bed provides sample-preparation/purification and the other serves as an analytical chromatography column; and the beds are arranged such that fluid flows first through the sample-preparation/purification sorbent bed and then to the sorbent bed configures as an analytical chromatography column.

It is to be understood that the inner diameters of the first inner tube, second inner tube and support tube can be the same or different and that in various embodiments the first inner tube has a smaller inner diameter than the second inner tube and in others the first inner tube has a larger inner diameter than the second inner tube. It is also to be understood that the inner and outer diameters of the third inner tube and fourth inner tube (when both are present) can be the same or different and that in various preferred embodiments the third inner tube has substantially the same inner diameter as the support tube or the fourth inner tube if present.

It is to be understood that the present inventions in various aspects and embodiments encompass a variety of tube configurations and structures. For example, referring to FIGS. 3A-3C, in various embodiments a tubing or chromatographic column assembly 300, 301, 302, comprises a first inner tube 310, 310', a second inner tube 320, 320' both disposed within an outer tube 340, and a support tube 327, 327', 327" disposed within the second inner tube. The first inner tube having a first end 312 and a second end 314 and the second inner tube having a first end 322 and a second end 324. The first end 312 of the first inner tube abuts against the second end 324 of the second inner tube. The area of contact between the second end 324 and the first end 312 defines an end interface 330.

In various embodiments, the outer tube 340 has at least two radial crimps, a first radial crimp 342 and a second radial crimp 344. The first radial crimp 342 is at a longitudinal location along the outer tube in a direction away from the end interface 330 towards the first end 322 of the second inner tube at a distance x from the end interface and the second radial crimp 344 is at a longitudinal location along the outer tube away from the end interface in the direction of the first radial crimp at a distance further away from the end interface than the first radial crimp, preferably at a distance of 2x, and preferably between the first radial crimp 342 and the first end 322 of the second tube. The distance x is such that deformation of the outer tube 340 to create the first radial crimp 342 forms a fluid-tight seal between the second end 324 of the second inner tube and the first end 312 of the first inner tube at the end interface 330.

In various embodiments, the outer tube 340 employs a third radial crimp 346 to affix the first inner tube to the outer tube. It is to be understood that other means can be employed to affix the first inner tube to the outer tube, including, but not limited to, mechanical means (such as, e.g., a nut, fitting, block, ring, ferrule), chemical means (such as, e.g., epoxy, resin, glue), alteration means (such as, e.g., softening or partially melting the first inner tube to the outer tube or an intermediate tube to the outer surface of the first inner tube and the inner surface of the outer tube), or other means that substantially prevents the first inner tube from moving in a longitudinal direction away from the end interface. Although a third radial crimp is illustrated in the Figures it is thus to be understood that a third radial crimp is not necessary to practice the present inventions, rather many means can be employed to affix the first inner tube to the outer tube prior to or during formation of the first radial crimp.

Figure 3A:
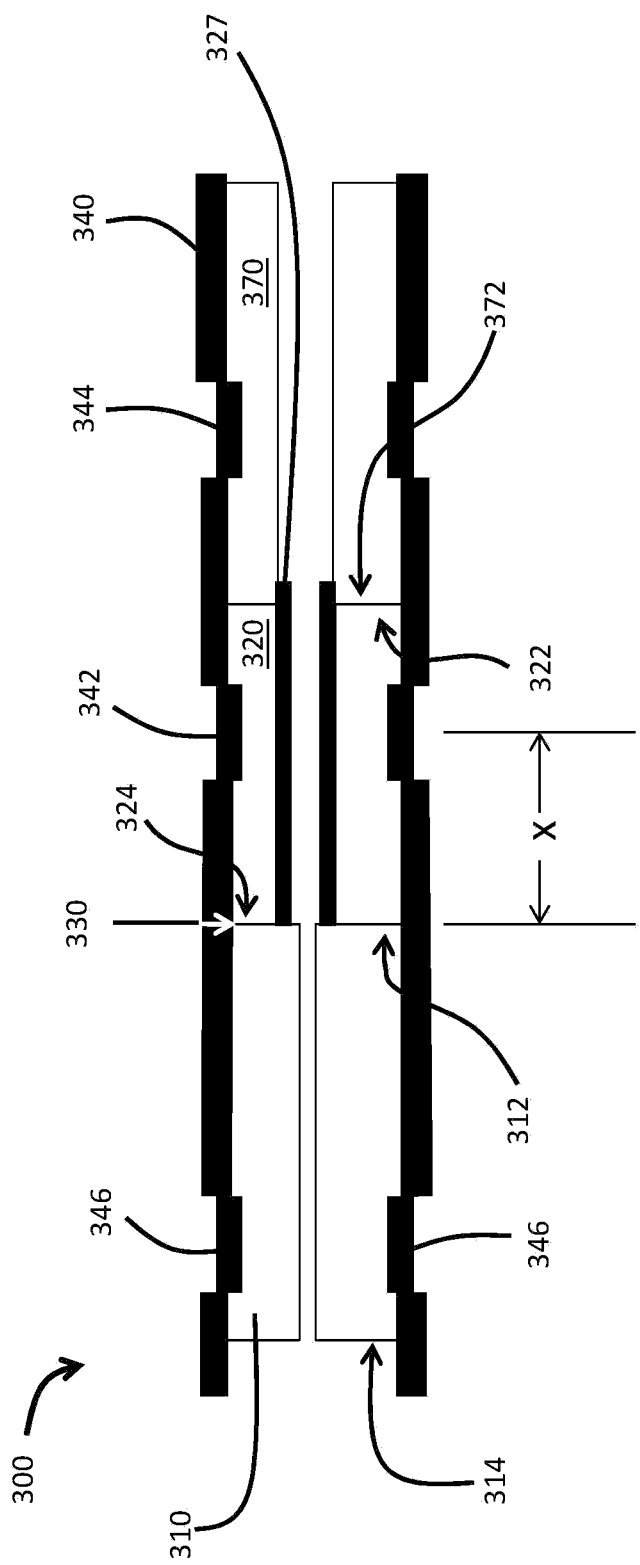
FIGS. 3A-3C are schematic cross-sectional illustrations of a tubing assembly and/or chromatographic column assembly according to various embodiments of the inventions illustrating further inner tube and support tube configurations.

Referring to FIG. 3A, in various embodiments, the second inner tube does not extend to the second radial crimp. In various embodiments an end tube 370 is abutted against the first end 322 of the second inner tube 320 and a second radial crimp 344 holds the end tube in place, and in various embodiments provides a radial fluidic seal between the inner surface of the outer tube and the outer surface of the end tube, the inner surface of the end tube and the outer surface of the support tube, or both. In various embodiments, the support tube extends past the second inner tube-end tube interface, and preferably past the second radial crimp. In various embodiments, the second radial crimp is positioned a distance from the second inner tube-end tube interface such that a seal is formed between the end of the end tube abutting the first end of the second inner tube (a more detailed discussion of such various embodiments are provided in the context of FIG. 4).

Figure 3B:
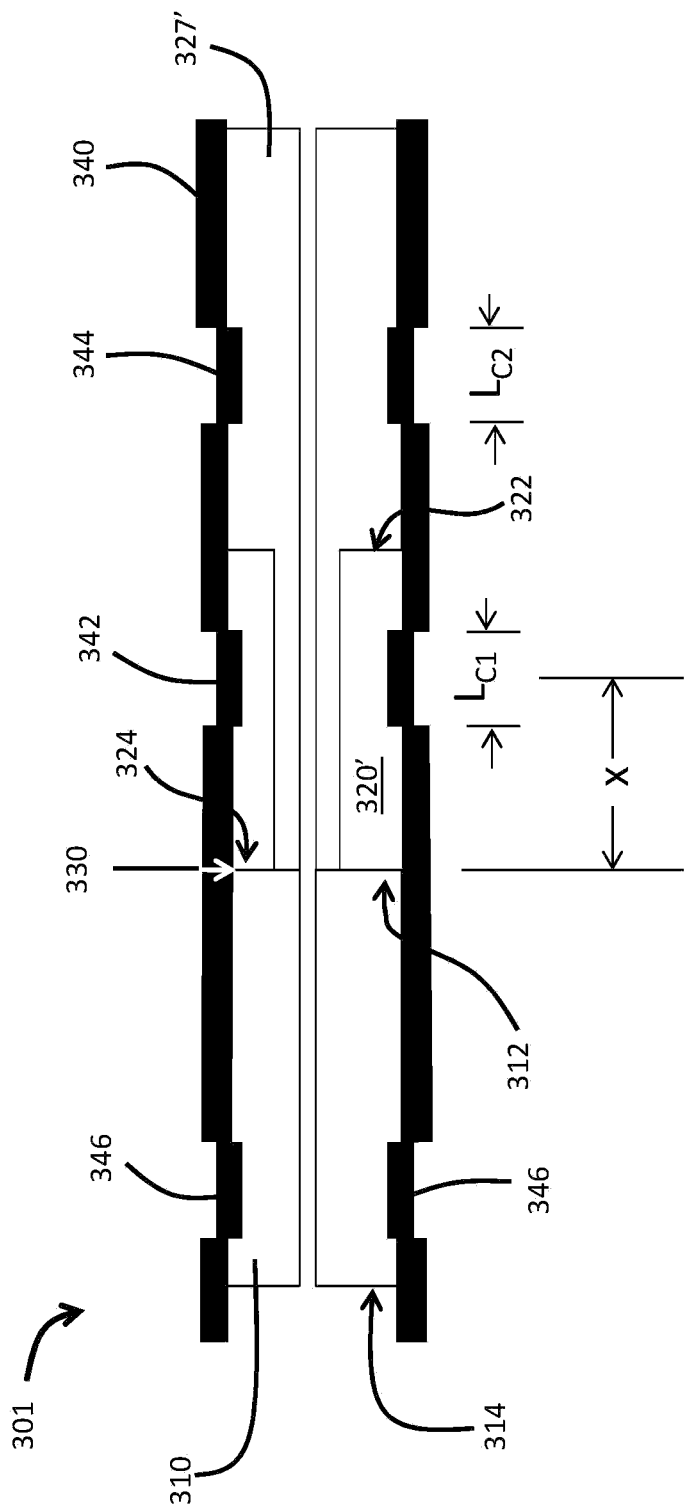

Referring to FIG. 3B, in various embodiments the inner tubes do not have a constant outer and/or inner diameter. For example, in various embodiments, the support tube 327' has a smaller outer diameter portion that fits into the lumen of the second inner tube 320'. Similar arrangements with respect to the first inner tube and the third inner tube are also encompassed by various embodiments of the present inventions.

It is to be understood that multiple tubes can be disposed within each other in various embodiments of the assemblies of the present inventions. For example, referring to FIG. 3C, in various embodiments, a third inner tube 350 is disposed in the lumen of the first inner tube 310' and an additional inner tube (or tubes) 380 is disposed within the third inner tube. The additional inner tube can be made from a variety of materials, including, but not limited to a metal, such as stainless steel, or a polymeric material.

Figure 3C:
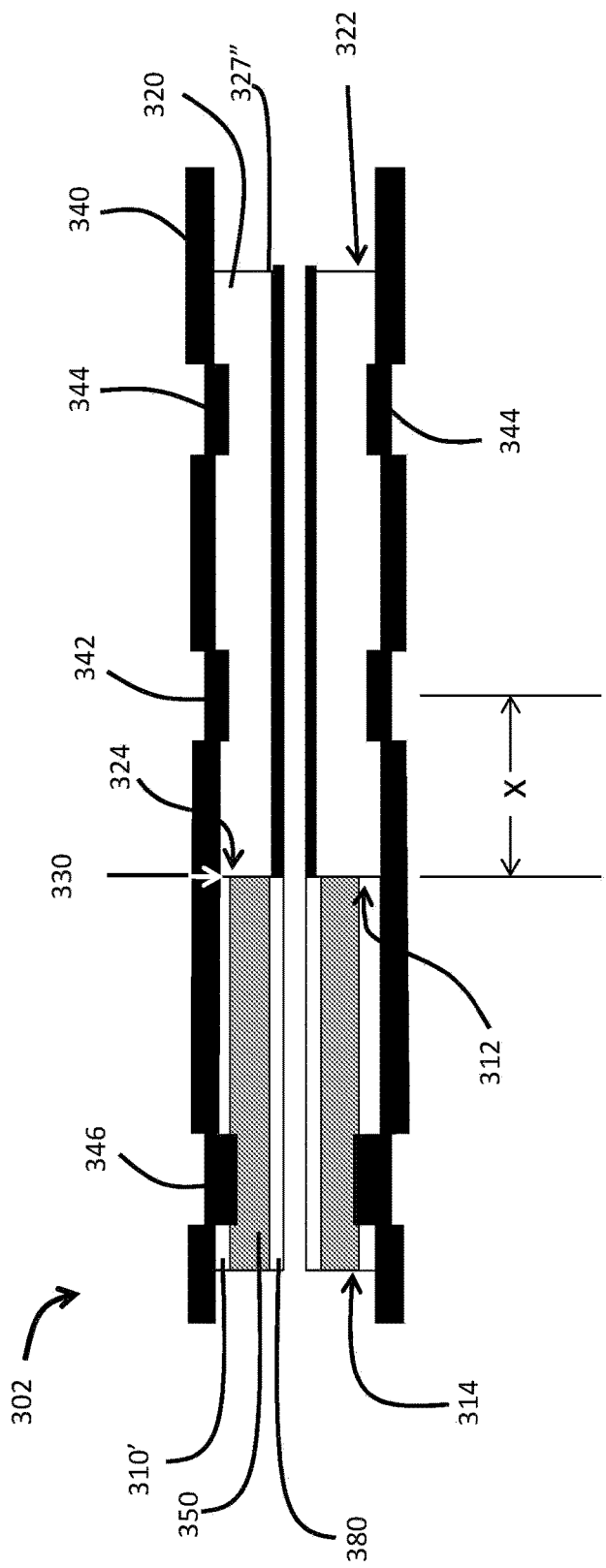

It is to be understood that the although FIGS. 3A-3C do not illustrate a sorbent bed disposed within that assembly, that a chromatographic column assemblies are encompassed by FIGS. 3A-3C by inclusion of a sorbent bed within a lumen, for example, of one of more of the first inner tube, a third inner, and the support tube following the teachings, discussion and disclosures provided herein.

The teachings with respect to the embodiments and structures described in the context of FIGS. 1A-1F, 2A-2D and FIGS. 3A-3C, can be applied to embodiments comprising multiple fluidic face seals. For example, it is to be understood that in the context of FIG. 4, for example, the teachings with respect to second inner tubes can be applied to the sealing tubes, the teachings with respect to the first radial crimps can be applied to the sealing radial crimps, the teachings with respect to the second radial crimp can be applied to the locking radial crimps, the teachings with respect to the first inner tube can be applied to the stationary tube, the teachings with respect to the third radial crimp can be applied to the affixing radial crimp, etc.

Figure 4:
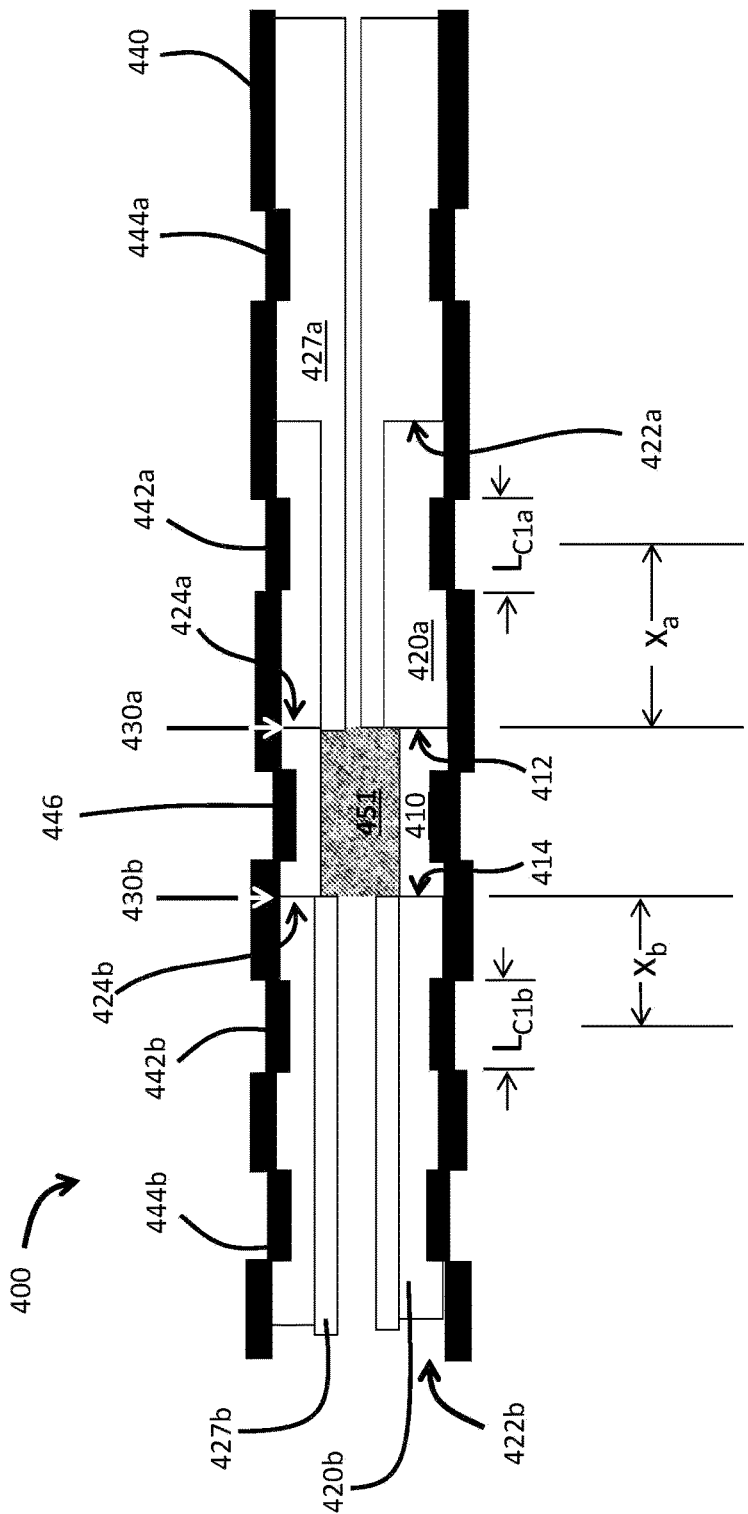
FIG. 4 is a schematic cross-sectional illustration of a chromatographic column assembly according to various embodiments of the inventions illustrating the use of multiple fluidic face seals according to various embodiments of the inventions.

In various aspects and embodiments, the present inventions tubing and chromatographic column assemblies with multiple fluidic face seals. Referring to FIG. 4, in various embodiments an assembly 400 comprises a stationary tube 410, a first sealing tube 420a, and a second sealing tube 420b, all disposed within an outer tube 440, and a first support tube 427a disposed within the lumen of the first sealing tube 420a and a second support tube 427b disposed within the lumen of the second sealing tube 420b. The stationary tube having a first end 412 and a second end 414, the first sealing tube having a first end 422a and a second end 424a, and the second sealing tube having a first end 422b and a second end 424b. The first end 412 of the stationary tube abuts against the second end 424a of the first sealing tube 420a and the second end 414 of the stationary tube abuts the second end 424b of the second sealing tube 420b. The area of contact between the stationary tube first end 412 and the second end 424a of the first sealing tube defines a first end interface 430a, and the area of contact between the stationary tube second end 414 and the second end 424b of the second sealing tube defines a second end interface 430b.

In various preferred embodiments of a chromatographic column assembly, a sorbent bed 451 is disposed in the lumen of the stationary tube. In various embodiments a sorbent bed is disposed in one or more of: the lumen of the first support tube (or the lumen of a tube within the lumen of the first support tube), the lumen of the second support tube (or the lumen of a tube within the lumen of the second support tube), and the lumen of the stationary tube (or the lumen of a tube within the lumen of the stationary tube).

In various embodiments, the outer tube 440 has at least two sealing radial crimps and two locking radial crimps. The first sealing radial crimp 442a is at a longitudinal location along the outer tube in a direction away from the first end interface 430a towards the first end 422a of the first sealing tube 420a at a distance $x_a$ from the first end interface 430a. The second sealing radial crimp 442b is at a longitudinal location along the outer tube in a direction away from the second end interface 430b towards the first end 422b of the second sealing tube 420b at a distance $x_b$ from the second end interface 430b. The distance $x_a$ is such that deformation of the outer tube 440 by the first sealing radial crimp 442a forms a fluid-tight seal between the second end 424a of the first sealing tube and the first end 412 of the stationary tube at the first end interface 430a, and the distance $x_b$ is such that deformation of the outer tube 440 by the second sealing radial crimp 442b forms a fluid-tight seal between the second end 424b of the second sealing tube and the second end 414 of the stationary tube at the second end interface 430b.

In addition, in preferred embodiments, the first sealing radial crimp, the second sealing radial crimp, or both, also provide radial sealing. In various embodiments, the first sealing radial crimp forms a radial fluidic seal between one or more of: (a) the inner surface of the first sealing tube and the outer surface of the first support tube; (b) the inner surface of the outer tube and the outer surface of the first sealing tube; and (c) between the contacting surfaces of all tubes within the lumen of the outer tube at the location of the first sealing radial crimp. In various embodiments, the second sealing radial crimp also forms a radial fluidic seal between one or more of: (a) the inner surface of the second sealing tube and the outer surface of the second support tube; (b) the inner surface of the outer tube and the outer surface of the second sealing tube; and (c) between the contacting surfaces of all tubes within the lumen of the outer tube at the location of the first sealing radial crimp.

The distances $x_a$ and $x_b$ can be determined using the teachings herein with respect to the distance x. It is to be understood that the distances $x_a$ and $x_b$ can differ. For example, in various embodiments the distances $x_a$ and $x_b$ are distances at which the stress applied by the respective sealing tube end face at the against the respective end interface (e.g., the first end interface for the first sealing radial crimp and the second end interface for the second sealing radial crimp) is between about between about 70 MPa to about 200 MPa, and preferably between about 100 MPa and about 150 MPa. Without being held to theory, the stress applied against the end interface is related to the distance ($x_a$ or $x_b$), the circumferential stress created by the sealing radial crimp and the Young's modulus of the respective sealing tube material. The circumferential stress applied by a sealing radial crimp is in turn determined primarily by the crimp depth ($\Delta_{1a}$ for the first sealing radial crimp; and $\Delta_{1b}$ for the second sealing radial crimp) and sealing radial crimp length ($L_{C1a}$ for the first sealing radial crimp; and $L_{C1b}$ for the second sealing radial crimp). For example, in various embodiments where, for example, a first sealing tube is a polyether ether ketone (PEEK) polymeric tube with outer diameter of about 1575 micrometers (62 thousandths of an inch, 0.062") and an inner diameter of about 711 micrometers (28 thousandths of an inch, 0.028"), with a first sealing radial crimp of depth between about 0.003 inches and about 0.01 inches, and a first sealing radial crimp length between about 0.05 inches and about 0.125 inches, the distance $x_a$, is between about 3.6 millimeters to about 28 millimeters (in U.S. English units between about 0.14 to about 1.1 inches), and preferably about 5 millimeters (about 0.20 inches), with a crimp depth of about 0.15 mm (0.006 inches) and a crimp length of about 1.58 mm (0.062 inches).

In various preferred embodiments, to produce a fluidic face seal at an end interface sufficient to withstand an operating fluidic pressure greater than about 15,000 psi (about 100 MPa), a sealing radial crimp distance ($x_a$ and/or $x_b$) is chosen to result in sealing stress at the end interface of about one and a half times (1.5×) the operating fluidic pressure.

The assembly further comprises a first locking radial crimp 444a and a second locking radial crimp 444b, where the first locking radial crimp is at a longitudinal location along the outer tube in the direction of the first sealing radial crimp and further away from the first end interface 430a than the first sealing radial crimp 442a, and the second locking radial crimp is at a longitudinal location along the outer tube in the direction of the second sealing radial crimp and further away from the second end interface 430b than the second sealing radial crimp 442b. In various preferred embodiments, the first locking radial crimp is at a distance equal to about twice $x_a$ from the first end interface, and the second locking radial crimp is at a distance equal to about twice $x_b$ from the second end interface.

The outer tube 440 is preferably affixed to the stationary tube 410. In various embodiments an affixing radial crimp 446 is used to affix the outer tube to the stationary tube. It is to be understood that other means can be employed to affix the stationary tube to the outer tube, including, but not limited to, mechanical means (such as, e.g., a nut, fitting, block, ring, ferrule), chemical means (such as, e.g., epoxy, resin, glue), alteration means (such as, e.g., softening or partially melting the first inner tube to the outer tube or an intermediate tube to the outer surface of the first inner tube and the inner surface of the outer tube), or other means that substantially prevents the stationary tube from moving in a longitudinal direction away from an end interface during formation of a sealing radial crimp. Thus, it is to be understood that a radial crimp is not necessary to practice the present inventions; rather many means can be employed to affix the stationary tube to the outer tube prior to or during formation of a sealing radial crimp.

It is to be understood that the sealing tubes, support tubes, additional tubes, etc. can take on a variety of shapes and they are not limited to the sealing tube and support tube shapes illustrated in FIG. 4.

In various embodiments, the polymeric material of a sealing tube has a Young's modulus in the range between about 0.4 to about 5 gigapascals (GPa). In various embodiments the polymeric material has a Young's modulus in the range between about 0.4 to about 1 GPa such as, for example, polytetrafluoroethylene (PTFE) polymers, high density polyethylene (HDPE) polymers and the like. In various embodiments the polymeric material has a Young's modulus in the range between about 1 to about 2 GPa such as, for example, polypropylene (PP) polymers and the like. In various embodiments the polymeric material has a Young's modulus in the range between about 2 to about 3 GPa such as, for example, polyethylene terephthalate (PET) polymers and the like. In various embodiments the polymeric material has a Young's modulus in the range between about 3 to about 4 GPa such as, for example, polyether ether ketone (PEEK) polymers and the like. In various embodiments the polymeric material has a Young's modulus in the range between about 4 to about 5 GPa such as, for example, polyaryletherketone (PAEK) polymers and the like.

A support tube can be made of a variety of materials provided that the support tube is more resistant to deformation due to compression than the sealing tube in which lumen it is disposed. In various embodiments, a support tube is comprised of one or more of a ceramic, a glass or metal. A preferred glass for the support tube material is a fused silica glass and a preferred metal for the support tube is a stainless steel.

In various aspects, also provided are methods of making a fluidic connection between two fluidic conduits to create, for example, the tubing assemblies and chromatographic column assemblies disclosed herein. It is to be understood that the structures to be achieved include, but are not limited to, those described in relation to FIGS. 1A-1F, FIGS. 2A-2D, FIGS. 3A-3C and FIG. 4.

In various aspects the present inventions, the methods operate on a second inner tube made of a polymeric material, an outer tube made of a metal (e.g., a stainless steel), or other suitable material that is ductile and exhibits non-elastic deformation similar to metals, and a support tube disposed in the lumen of the second inner tube, the support tube, the support tube being more resistant to deformation by radial compression than the second inner tube. A wide range of polymeric materials are suitable for use as the second inner tube material and are preferably chosen based on the Young's modulus of the material.

In various embodiments, the polymeric material has a Young's modulus in the range between about 0.4 to about 5 gigapascals (GPa). In various embodiments the polymeric material has a Young's modulus in the range between about 0.4 to about 1 GPa such as, for example, polytetrafluoroethylene (PTFE) polymers, high density polyethylene (HDPE) polymers and the like. In various embodiments the polymeric material has a Young's modulus in the range between about 1 to about 2 GPa such as, for example, polypropylene (PP) polymers and the like. In various embodiments the polymeric material has a Young's modulus in the range between about 2 to about 3 GPa such as, for example, polyethylene terephthalate (PET) polymers and the like. In various embodiments the polymeric material has a Young's modulus in the range between about 3 to about 4 GPa such as, for example, polyether ether ketone (PEEK) polymers and the like. In various embodiments the polymeric material has a Young's modulus in the range between about 4 to about 5 GPa such as, for example, polyaryletherketone (PAEK) polymers and the like.

In one aspect, the invention features a method of forming a fluidic connection between two fluidic conduits. The method can operate on a tubing assembly comprised of an outer tube having disposed within a first inner tube and a second inner tube, where the first inner tube is affixed to the outer tube, and where a support tube more resistant to deformation by radial compression than the second inner tube is disposed within the lumen of the second inner tube. An outer tube is provided having disposed therein a first inner tube, a second inner tube, and a support tube disposed in the second inner tube, where the first inner tube is affixed to the outer tube. The second inner tube is abutted against the first inner tube. For the sake of more exact expression, the first inner tube and second inner tubes both have first and second ends and the second end of the second inner tube is abutted against the first end of the first inner tube. The area of contact between the second end of the second inner tube and the first end of the first inner tube defines an end interface.

A distance x, in a longitudinal direction away from the end interface towards the first end of the second inner tube, is selected for formation of a first radial crimp. The distance x is selected such that upon formation of the first radial crimp (e.g. by circumferential deformation of the outer tube) the material of the second inner tube is extruded in a longitudinal direction from the location of the first radial crimp towards the end interface to create a fluid-tight seal between the second end of the second inner tube and the first end of the first inner tube at the end interface.

Without being held to theory, in various embodiments the distance x is a distance at which the stress applied by the second end of the second inner tube against the end interface is between about between about 70 MPa to about 200 MPa, and preferably between about 100 MPa and about 150 MPa, (roughly about 10,000 to about 30,000 psi, preferably between about 15,000 psi to about 22,000 psi). Without being held to theory, the stress applied against the endface is related to the distance x, the circumferential stress created by the first radial crimp and the Young's modulus of the second inner tube. The circumferential stress applied by the first crimp is in turn determined primarily by the first radial crimp depth ($\Delta_1$) and first radial crimp length ($L_{C1}$). The greater fluidic pressure the seal is projected to withstand, the shorter the distance x from the range of distances should be selected and/or a greater first crimp volume ($V_{C1}$) selected ($V_{C1}$ being proportional to $\Delta_1 \times L_{C1}$). However, it is to be understood, according to the present inventions, that too short of a distance x will not provide enhanced sealing but rather could result in unacceptable deformation of the second inner tube in the radial direction, and/or exert pressure sufficient to crack a silica tube in the lumen of the second inner tube and/or the first inner tube. Accordingly, the inventors have discovered a range wherein sufficient sealing can be made to occur without undue radial deformation or imposition of undue stress on silica tubes near the sealing region.

Without being held to theory, the distance x according to the present inventions is directly proportional to the volume displaced by the first radial crimp and the distance x is inversely proportional to the end interface pressure (sealing pressure) desired. In various preferred embodiments, to produce a fluidic face seal at the end interface sufficient to withstand an operating fluidic pressure greater than about 15,000 psi (about 100 MPa) and preferably less than about 22,000 psi, the distance x is selected to result in sealing stress at the end interface of about one (1×) and about two (2×) times the operating fluidic pressure, and preferably about one and a half times (1.5×) the operating fluidic pressure.

After selection of the distance x, the outer tube is deformed to create the first radial crimp (having a crimp depth $\Delta_1$ and a crimp length $L_{C1}$) at the distance x from the end interface, and then the outer tube is deformed to create a second radial crimp (having a crimp depth $\Delta_2$ and a crimp length $L_{C2}$) at a longitudinal location in the direction of the first radial crimp and further away from the end interface than the first radial crimp, preferably at a location a distance about twice x from the end interface, and in various embodiments between the end interface and the first end of the second inner tube. In various embodiments, the second radial crimp serves to further hold the second inner tube motionless within the outer tube. In various embodiments, the second radial crimp provides a fluidic seal between the outer surface of the second inner tube and the inner surface of the outer tube, the inner surface of the second inner tube and the outer surface of the support tube, or both; however, it is to be understood that the second radial crimp is not required to provide a fluidic seal as a fluidic seal is formed over at least a portion of the end interface between the first end of the first inner tube and the second end of the second inner tube. In addition, in various embodiments, the first radial crimp also forms a radial fluidic seal between one or more of: (a) the inner surface of the second inner tube and the outer surface of the support tube; (b) the inner surface of the outer tube and the outer surface of the second inner tube; and (c) between the contacting surfaces of all tubes within the lumen of the outer tube at the location of the first radial crimp.

In one aspect, the invention features a method of forming a chromatographic column assembly. An outer tube is provided having disposed therein a first inner tube and a second inner tube, where the first inner tube is affixed to the outer tube, and where a support tube, more resistant to deformation by radial compression than the second inner tube, is disposed within the lumen of the second inner tube. The first inner tube can be affixed to the outer tube in many ways as described herein. Within the lumen of the first inner tube, the support tube, or both, is disposed a chromatographic media. The chromatographic media can, in various embodiments, be disposed within an additional inner tube. The chromatographic media is predisposed within lumen of the first or second inner tube, that is, it is disposed within the inner tube prior to the step of deforming the outer tube. In various embodiments, an additional inner tube is provided in both the first inner tube and support tube, that is, a third inner tube is predisposed in the lumen of the first inner tube and a fourth inner tube predisposed in the lumen of the support tube, and a chromatographic media or sorbent bed is disposed in the lumens of the third and fourth inner tubes.

The second inner tube is abutted against the first inner tube. The first inner tube and second inner tubes both have first and second ends and the second end of the second inner tube is abutted against the first end of the first inner tube. The area of contact between the second end of the second inner tube and the first end of the first inner tube defines an end interface.

A distance x, in a longitudinal direction away from the end interface towards the first end of the second inner tube, is selected for formation of a first radial crimp. The distance x is selected, as previously described herein, such that upon formation of the first radial crimp (e.g. by circumferential deformation of the outer tube) the material of the second inner tube is extruded in a longitudinal direction from the location of the first radial crimp towards the end interface to create a fluid-tight seal between the second end of the second inner tube and the first end of the first inner tube at the end interface. As described herein, in various embodiments, the distance x is selected such that a stress of about between about 70 MPa to about 200 MPa, and preferably between about 100 MPa and about 150 MPa, is applied to the first end of the first inner tube upon deformation of the outer tube to create the first radial crimp. In various embodiments, the distance x is selected to result in sealing stress at the end interface of about one and a half times (1.5×) the operating fluidic pressure.

After selection, the outer tube is deformed to create the first radial crimp at the distance x from the end interface, and then in various embodiments the outer tube is deformed to create a second radial crimp at a longitudinal location in the direction of the first radial crimp and further away from the end interface than the first radial crimp, preferably at a location a distance about twice x from the end interface, and in various embodiments between the end interface and the first end of the second inner tube. In various embodiments, the second radial crimp serves to further hold the second inner tube motionless within the outer tube. In various embodiments, the second radial crimp provides a fluidic seal between the outer surface of the second inner tube and the inner surface of the outer tube, the inner surface of the second inner tube and the outer surface of the support tube, or both. It is to be understood that the second radial crimp is not required to provide a fluidic seal as a fluidic seal is formed over at least a portion of the end interface between the first end of the first inner tube and the second end of the second inner tube. In addition, in various embodiments, the first radial crimp also forms a radial fluidic seal between the inner surface of the second inner tube and the outer surface of the support tube.

In various aspects also provided are methods of making tubing and chromatographic column assemblies comprising multiple face seals according to the present teachings. In various embodiments, the methods operate on an assembly comprised of an outer tube having disposed within a stationary tube, a first sealing tube having in the lumen thereof a first support tube, and a second sealing tube having in the lumen thereof a second support tube, where the first inner tube is affixed to the outer tube, and where the support tubes are more resistant to deformation by radial compression than the sealing tubes in which they are disposed.

An outer tube having affixed therein a stationary tube is provided. In various embodiments of methods of making a chromatographic assembly the stationary tube has disposed in its lumen a sorbent bed. The first sealing tube is abutted against the first end of the stationary tube. The area of contact between end of the first sealing tube and the first end of the stationary tube defines a first end interface.

A first distance $x_a$ is selected for formation of a first sealing radial crimp, the distance $x_a$ being measured from the first end interface in the direction towards the first sealing tube. The distance $x_a$ is selected based on the same teachings, disclosures and discussions set forth herein with respect to the distance x.

The outer tube is deformed to create the first sealing radial crimp (having a crimp depth $\Delta_{1a}$ and a crimp length $L_{C1a}$) at the distance $x_a$ from the first end interface. The first sealing radial crimp extrudes material of the first sealing tube in a longitudinal direction from the location of the first sealing radial crimp towards the first end interface to create a fluid-tight seal between the end of the first sealing tube and the first end of the stationary tube at the first end interface. In addition, in preferred embodiments, the first sealing radial crimp also forms a radial fluidic seal between one or more of: (a) the inner surface of the first sealing tube and the outer surface of the first support tube; (b) the inner surface of the outer tube and the outer surface of the first sealing tube; and (c) between the contacting surfaces of all tubes within the lumen of the outer tube at the location of the first sealing radial crimp.

In various embodiments, the outer tube is then deformed to create a first locking radial crimp (prior to the formation of the second sealing radial crimp) at a longitudinal location in the direction of the first sealing radial crimp and further away from the first end interface than the first sealing radial crimp, preferably at a location a distance about twice $x_a$ from the first end interface. In various embodiments, the first locking radial crimp forms a radial fluidic seal between one or more of: (a) the inner surface of the first sealing tube and the outer surface of the first support tube; (b) the inner surface of the outer tube and the outer surface of the first sealing tube; and (c) between the contacting surfaces of all tubes within the lumen of the outer tube at the location of the first locking radial crimp.

The second sealing tube is abutted against the second end of the stationary tube. The area of contact between end of the second sealing tube and the second end of the stationary tube defines a second end interface. It is to be understood that in various embodiments, the second sealing tube is abutted against the second end of the stationary tube prior to formation of the first sealing radial crimp.

A second distance $x_b$ is selected for formation of a second sealing radial crimp, the distance $x_b$ being measured from the second end interface in the direction towards the second sealing tube. The distance $x_b$ is selected based on the same teachings, disclosures and discussions set forth herein with respect to the distance x.

The outer tube is deformed to create a second sealing radial crimp (having a crimp depth $\Delta_{1b}$ and a crimp length $L_{C1b}$) at the distance $x_b$ from the first end interface. The second sealing radial crimp extrudes material of the second sealing tube in a longitudinal direction from the location of the second sealing radial crimp towards the second end interface to create a fluid-tight seal between the end of the second sealing tube and the second end of the stationary tube at the second end interface. In addition, in preferred embodiments, the second sealing radial crimp also forms a radial fluidic seal between one or more of: (a) the inner surface of the second sealing tube and the outer surface of the second support tube; (b) the inner surface of the outer tube and the outer surface of the second sealing tube; and (c) between the contacting surfaces of all tubes within the lumen of the outer tube at the location of the first sealing radial crimp.

In various embodiments, the outer tube is then deformed to create a second locking radial crimp at a longitudinal location in the direction of the second sealing radial crimp and further away from the second end interface than the second sealing radial crimp, preferably at a location a distance about twice $x_b$ from the second end interface. In various embodiments, the second locking crimp forms a radial fluidic seal between one or more of: (a) the inner surface of the second sealing tube and the outer surface of the second support tube; (b) the inner surface of the outer tube and the outer surface of the second sealing tube; and (c) between the contacting surfaces of all tubes within the lumen of the outer tube at the location of the second locking radial crimp.

In various embodiments of methods of making a chromatographic assembly, one or more sorbent beds are disposed in the lumen of one or more of the stationary tube, the first support tube, and the second support tube. In various embodiments, one or more intermediate tubes are disposed in the lumens of one or more of the stationary tube, the first support tube, and the second support tube, and one or more sorbent beds are disposed in the lumen of one or more intermediate tubes.

Selection of the distance x applicable to the various aspects of the present invention shall now be illustrated by way of the following non-limiting examples. It is to be understood that although the following examples are discussed in the context of a first radial crimp and second inner tube, they can be applied equally well to the embodiments including multiple face seals; for example, determination of $x_a$ and/or $x_b$, where a sealing tube is equated to the second inner tube and a sealing radial crimp is equated to the first radial crimp.

Example 6: Formation of a face seal able to withstand fluidic pressures greater than about 15,000 psi and less than about 22,000 psi. The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 711 micrometers (28 thousandths of an inch, 0.028"). The first crimp depth is about 0.006 inches, and first crimp length about 0.062 inches. A distance of about 8.6 millimeters (about 0.34 inches) is selected for x.

Example 7: Formation of a face seal able to withstand fluidic pressures greater than about 15,000 psi and less than about 22,000 psi. The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 381 micrometers (15 thousandths of an inch, 0.015"). The first crimp depth is about 0.006 inches, and first crimp length about 0.062 inches. A distance of about 7.4 millimeters (about 0.29 inches) is selected for x.

Example 8: Formation of a face seal able to withstand fluidic pressures greater than about 15,000 psi and less than about 22,000 psi. The second inner tube is a polyethylene terephthalate (PET) polymeric tube with a Young's modulus (aka modulus of elasticity) of about 2.8 GPa, an outer diameter of about 1575 micrometers (62 thousandths of an inch, 0.062") and an inner diameter of about 711 micrometers (28 thousandths of an inch, 0.028"). The first crimp depth is about 0.007 inches, and first crimp length is about 0.062 inches. A distance of about 7.9 millimeters (about 0.31 inches) is selected for x.

Example 9: Formation of a face seal able to withstand fluidic pressures greater than about 15,000 psi and less than about 22,000 psi. The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 711 micrometers (28 thousandths of an inch, 0.028"). The first crimp depth is about 0.01 inches, and first crimp length about 0.062 inches. A distance of about 13.7 millimeters (about 0.54 inches) is selected for x.

Example 10: Formation of a face seal able to withstand fluidic pressures greater than about 15,000 psi and less than about 22,000 psi. The second inner tube is a polyether ether ketone (PEEK) polymeric tube with a Young's modulus (aka modulus of elasticity) of about 3.5 GPa, an outer diameter of about 1575 micrometers (62 thousandths of an inch, 0.062") and an inner diameter of about 711 micrometers (28 thousandths of an inch, 0.028"). The first crimp depth is about 0.01 inches, and first crimp length about 0.1 inches. A distance of about 22 millimeters (about 0.87 inches) is selected for x.

While the invention has been shown and described with reference to specific preferred embodiments, it should be understood by those skilled in the art that various changes in form and detail may be made therein without departing from the scope of the invention as defined by the following claims.

What is claimed is:

1. A tubing assembly, comprising:
   an outer tube;
   a first inner tube disposed inside the outer tube and affixed to the outer tube, the first inner tube having a first end and a second end;
   a second inner tube disposed inside the outer tube, the second inner tube having a first end and a second end, the second end of the second inner tube abutting against the first end of the first inner tube, the area of contact between the second end of the second inner tube and the first end of the first inner tube defining an end interface; and
   a support tube disposed within the second inner tube, the support tube comprised of a material having a Young's modulus greater than the Young's modulus of the material comprising the second inner tube;
   wherein, the outer tube has a first radial crimp and a second radial crimp;
   the first radial crimp having a length $L_{C1}$ and being at a longitudinal location along the outer tube in a direction away from the end interface towards the first end of the second inner tube at a distance x from the end interface; and the second radial crimp being at a longitudinal location along the outer tube between the first radial crimp and the first end of the second inner tube,
wherein the distance x is such that deformation of the outer tube to create the first radial crimp forms a fluid-tight seal between the second end of the second inner tube and the first end of the first inner tube at the end interface; and
wherein the support tube extends from at least the first end of the first inner tube in a longitudinal direction away from the first end of the first inner tube at least a distance $x+L_{C1}$.

2. The tubing assembly of claim 1 wherein the outer tube has a third radial crimp being at a longitudinal location along the outer tube in a direction away from the end interface towards the second end of the first inner tube.

3. The tubing assembly of claim 1 wherein the inner diameter of the first inner tube is different from the inner diameter of the second inner tube.

4. The tubing assembly of claim 1 wherein the outer diameter of the first inner tube is different from the outer diameter of the second inner tube.

5. The tubing assembly of claim 1 wherein the first inner tube comprises a polymeric material.

6. The tubing assembly of claim 1 wherein the distance x is determined by the distance sufficient to apply a stress between about 100 MPa to about 200 MPa against the first end of the first tube.

7. The tubing assembly of claim 1 further comprising an additional inner tube disposed within one or more of the first inner tube and the support tube.

8. The tubing assembly of claim 7 wherein the additional inner tube comprises a third inner tube disposed in the lumen of the first inner tube.

9. The tubing assembly of claim 8 wherein the first inner tube and the third inner tube are formed as an integrated structure.

10. The tubing assembly of claim 7 wherein the additional inner tube comprises a fourth inner tube disposed in the lumen of the support tube.

11. The tubing assembly of claim 10 wherein the support tube and the fourth inner tube are formed as an integrated structure.

12. The tubing assembly of claim 7 wherein an additional inner tube is disposed within both the first inner tube and the support tube.

13. The tubing assembly of claim 12 wherein both additional inner tubes comprise fused silica.

14. The tubing assembly of claim 7 wherein at least one additional inner tube comprises fused silica.

15. The tubing assembly of claim 7 wherein at least one additional inner tube contains a sorbent bed disposed in the lumen of said additional inner tube.

16. The tubing assembly of claim 1 wherein the outer tube and one or more of the first inner tube and the second inner tube are formed as an integrated structure.

17. The tubing assembly of claim 1 wherein the support tube comprises a stainless steel.

18. A method of making a fluidic connection between two fluidic conduits comprising the steps of:
providing an outer tube having disposed therein a first inner tube and a second inner tube; the first inner tube being affixed to the outer tube and the first inner tube having a first end and a second end and the second inner tube having a first end and a second end; the second inner tube having disposed therein a support tube comprised of a material having a Young's modulus greater than the Young's modulus of the material comprising the second inner tube;
abutting the second end of the second inner tube against the first end of the first inner tube, the area of contact between the second end of the second inner tube and the first end of the first inner tube defining an end interface;
selecting a distance x at a longitudinal location along the outer tube in a direction away from the end interface towards the first end of the second inner tube for formation of a first radial crimp such that upon formation of the first radial crimp the material of the second inner tube is extruded in a longitudinal direction from the location of the second radial crimp towards the end interface applying a stress between about 70 MPa to about 200 MPa on the first end of the first inner tube;
deforming the outer tube to create the first radial crimp at the distance x from the end interface; and
deforming the outer tube to create a second radial crimp at a longitudinal location between the first radial crimp and the first end of the second inner tube.

19. The method of making a fluidic connection between two fluidic conduits of claim 18 further comprising before the step of deforming the outer tube to create a first radial crimp the step of:
affixing the first inner tube to the outer tube by deforming the outer tube to create a third radial crimp at a longitudinal location along the outer tube in a direction away from the end interface towards the second end of the first inner tube.

20. The method of making a fluidic connection between two fluidic conduits of claim 18 wherein the inner diameter of the first inner tube is different from the inner diameter of the second inner tube.

21. The method of making a fluidic connection between two fluidic conduits of claim 18 wherein the outer diameter of the first inner tube is different from the outer diameter of the second inner tube.

22. A chromatographic column assembly, comprising:
an outer tube;
a first inner tube disposed inside the outer tube and affixed to the outer tube, the first inner tube having a first end and a second end;
a second inner tube disposed inside the outer tube, the second inner tube having a first end and a second end, the second end of the second inner tube abutting against the first end of the first inner tube, the area of contact between the second end of the second inner tube and the first end of the first inner tube defining an end interface;
a support tube disposed within the second inner tube, the support tube comprised of a material having a Young's modulus greater than the Young's modulus of the material comprising the second inner tube; and
a sorbent bed disposed in the lumen of the first inner tube or the lumen of the support tube;
wherein, the outer tube has a first radial crimp and a second radial crimp;
the first radial crimp having a length $L_{C1}$ and being at a longitudinal location along the outer tube in a direction away from the end interface towards the first end of the second inner tube at a distance x from the end interface; and
the second radial crimp being at a longitudinal location along the outer tube between the first radial crimp and the first end of the second inner tube, wherein the distance x is such that deformation of the outer tube to create the first radial crimp forms a fluid-tight seal between the second end of the second inner tube and the first end of the first inner tube at the end interface; and wherein the support tube extends from at least the first end of the first inner tube in a longitudinal direction away from the first end of the first inner tube at least a distance $x+L_{C1}$.

23. The chromatographic column assembly of claim 22 wherein the outer tube has a third radial crimp at a longitudinal location along the outer tube in a direction away from the end interface towards the second end of the first inner tube.

24. The tubing assembly of claim 22 wherein the inner diameter of the first inner tube is different from the inner diameter of the second inner tube.

25. The tubing assembly of claim 22 wherein the outer diameter of the first inner tube is different from the outer diameter of the second inner tube.

26. The chromatographic column assembly of claim 22 the distance x is determined by the distance sufficient to apply a stress between about 100 MPa to about 200 MPa against the first end of the first tube.

27. The chromatographic column assembly of claim 22 wherein the additional inner tube comprises a third inner tube disposed in the lumen of the first inner tube.

28. The chromatographic column assembly of claim 27 wherein the first inner tube and the third inner tube are formed as an integrated structure.

29. The chromatographic column assembly of claim 22 further comprising a fourth inner tube disposed within the lumen of the support tube and the sorbent bed is disposed within the lumen of the fourth inner tube.

30. The chromatographic column assembly of claim 22 wherein the additional inner tube comprises a third inner tube disposed in the lumen of the first inner tube and further comprising a fourth inner tube disposed in the lumen of the support tube.

31. The chromatographic column assembly of claim 30 wherein the sorbent bed is disposed in the lumen of the third inner tube and an additional sorbent bed is disposed in the lumen of the fourth inner tube.

32. The chromatographic column assembly of claim 31 wherein the sorbent bed in the lumen of the third inner tube comprises a sample preparation chromatographic media and the additional sorbent bed disposed in the lumen of the fourth inner tube comprises an analytical chromatographic media.

33. The chromatographic column assembly of claim 22 wherein the additional inner tube comprises fused silica.

34. The chromatographic column assembly of claim 22 wherein the sorbent bed comprises a chromatographic media.

35. The chromatographic column assembly of claim 22 wherein the first inner tube comprises a stainless steel.

36. The chromatographic column assembly of claim 22 wherein the support tube comprises a stainless steel.

37. The tubing assembly of claim 22 wherein the outer tube and one or more of the first inner tube and the second inner tube are formed as an integrated structure.

38. The chromatographic column assembly of claim 22 further comprising a ferrule disposed on the outer tube proximate to one end of the outer tube for engaging a coupling body at a fluid port.

39. A method of making a chromatographic column assembly comprising the steps of:

providing an outer tube having disposed therein a first inner tube and a second inner tube; the first inner tube being affixed to the outer tube and the first inner tube having a first end and a second end and the second inner tube having a first end and a second end;

providing a support tube comprised of a material having a Young's modulus greater than the Young's modulus of the material comprising the second inner tube;

providing a chromatographic media disposed in the lumen of the first inner tube or the lumen of the support tube;

abutting the second end of the second inner tube against the first end of the first inner tube, the area of contact between the second end of the second inner tube and the first end of the first inner tube defining an end interface;

selecting a distance x at a longitudinal location along the outer tube in a direction away from the end interface towards the first end of the second inner tube for formation of a first radial crimp such that upon formation of the first radial crimp the material of the second inner tube is extruded in a longitudinal direction from the location of the second radial crimp towards the end interface applying a stress between about 70 MPa to about 200 MPa on the first end of the first inner tube;

selecting a length $L_{C1}$ for the first radial crimp;

disposing within the second inner tube the support tube such that the support tube extends in a longitudinal direction away from the first end at least a distance $x+L_{C1}$ from the first end of the first inner tube;

deforming the outer tube to create the first radial crimp of length $L_{C1}$ at the distance x from the end interface; and deforming the outer tube to create a second radial crimp at a longitudinal location between the first radial crimp and the first end of the second inner tube.

40. The method of making a chromatographic column assembly of claim 39 further comprising before the step of deforming the outer tube to create a first radial crimp the step of:

affixing the first inner tube to the outer tube by deforming the outer tube to create a third radial crimp at a longitudinal location along the outer tube in a direction away from the end interface towards the second end of the first inner tube.

41. The method of making a chromatographic column assembly of claim 39 further comprising providing an additional inner tube.

42. The method of making a chromatographic column assembly of claim 41 wherein the additional inner tube comprises a third inner tube disposed in the lumen of the first inner tube.

43. The method of making a chromatographic column assembly of claim 41 wherein the additional inner tube comprises a fourth inner tube disposed in the lumen of the support tube.

44. The method of making a chromatographic column assembly of claim 41 wherein the additional inner tube comprises a third inner tube disposed in the lumen of the first inner tube and further comprising a fourth inner tube disposed in the lumen of the support tube and wherein the chromatographic media is disposed in the lumen of the fourth inner tube.

45. The method of making a chromatographic column assembly of claim 44 further comprising a sorbent bed disposed in the lumen of the third inner tube.

46. The method of making a chromatographic column assembly of claim 45 wherein the sorbent bed in the third inner tube comprises a sample-preparation chromatographic media and the chromatographic media in the fourth inner tube comprises an analytical chromatographic media.

* * * * *